United States Patent
Torgerson et al.

(10) Patent No.: US 9,545,521 B1
(45) Date of Patent: *Jan. 17, 2017

(54) IDENTIFICATION OF ELECTRODE COMBINATION FOR EFFICACIOUS ELECTRICAL STIMULATION THERAPY

(71) Applicant: Medtronic, Inc., Minneapolis, MN (US)

(72) Inventors: Nathan A. Torgerson, Andover, MN (US); Lynn A. Davenport, New Brighton, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 28 days.

This patent is subject to a terminal disclaimer.

(21) Appl. No.: 14/575,818

(22) Filed: Dec. 18, 2014

Related U.S. Application Data

(63) Continuation of application No. 13/796,529, filed on Mar. 12, 2013, now Pat. No. 8,918,184.

(51) Int. Cl.
*A61N 1/372* (2006.01)
*A61N 1/36* (2006.01)

(52) U.S. Cl.
CPC ......... *A61N 1/3727* (2013.01); *A61N 1/3605* (2013.01); *A61N 1/36017* (2013.01)

(58) Field of Classification Search
CPC A61N 1/3727; A61N 1/3605; A61N 1/36017; A61N 1/36185; A61N 1/37247; H04R 25/606; H04R 2225/023; G10L 21/0208; G10L 2021/02087
See application file for complete search history.

(56) References Cited

U.S. PATENT DOCUMENTS

| | | | |
|---|---|---|---|
| 5,376,103 A | | 12/1994 | Anderson et al. |
| 6,052,624 A | * | 4/2000 | Mann ............... A61N 1/37247 607/46 |
| 6,609,032 B1 | | 8/2003 | Woods et al. |

(Continued)

OTHER PUBLICATIONS

U.S. Appl. No. 14/579,408, by Nathan A. Torgerson, filed Dec. 22, 2014.

(Continued)

*Primary Examiner* — Catherine Voorhees
(74) *Attorney, Agent, or Firm* — Shumaker & Sieffert, P.A.

(57) ABSTRACT

One or more efficacious electrode combinations for delivering electrical stimulation therapy to a patient may be selected based on the delivery of electrical stimulation to the patient via a predefined set of test electrode combinations in a predetermined order. In some examples, the electrode combinations of the set are arranged in the predetermined order such that adjacent electrode combinations in the order include at least one shared anode electrode or cathode electrode. In addition, the electrode combinations in the predetermined order may define a predetermined sequence of electrode patterns, each electrode pattern defining a relative arrangement between one or more anodes and one or more cathodes of the respective electrode pattern. In some examples, the transition between electrode combinations in the predefined set is achieved by incrementally adjusting at least one of anodic amplitudes assigned to active anode electrodes or cathodic amplitudes assigned to active cathode electrodes.

37 Claims, 17 Drawing Sheets

(56) References Cited

U.S. PATENT DOCUMENTS

| | | |
|---|---|---|
| 7,463,928 B2 | 12/2008 | Lee et al. |
| 7,555,346 B1 | 6/2009 | Woods et al. |
| 7,617,002 B2 | 11/2009 | Goetz |
| 7,774,067 B2 | 8/2010 | Keacher et al. |
| 7,853,323 B2 * | 12/2010 | Goetz .................. A61N 1/3605 128/925 |
| 8,233,990 B2 | 7/2012 | Goetz |
| 8,918,184 B1 | 12/2014 | Torgerson et al. |
| 2002/0133198 A1 | 9/2002 | Kramer et al. |
| 2004/0158298 A1 | 8/2004 | Gliner et al. |
| 2005/0060009 A1 * | 3/2005 | Goetz ................ A61N 1/36185 607/48 |
| 2005/0222646 A1 | 10/2005 | Kroll et al. |
| 2009/0043351 A1 | 2/2009 | Sathaye et al. |
| 2009/0196472 A1 * | 8/2009 | Goetz .................. A61N 1/0551 382/128 |
| 2010/0106231 A1 | 4/2010 | Torgerson et al. |
| 2011/0196455 A1 | 8/2011 | Sieracki et al. |
| 2012/0022615 A1 | 1/2012 | Goetz et al. |
| 2012/0136409 A1 | 5/2012 | Goetz et al. |
| 2013/0338733 A1 | 12/2013 | Goddard et al. |
| 2014/0172046 A1 | 6/2014 | Kothandaraman et al. |
| 2014/0214120 A1 | 7/2014 | Simon et al. |

OTHER PUBLICATIONS

Prosecution History from U.S. Appl. No. 13/796,529, dated May 1, 2014 through Aug. 19, 2014, 59 pages.

\* cited by examiner

FIG. 6

| | A | B | C | D | E | F | G | H | I | J | K | L | M | N | O | P | Q | R | S | T | U | V | W | X | Y | Z | AA | BB | CC | DD | EE |
|---|---|---|---|---|---|---|---|---|---|---|---|---|---|---|---|---|---|---|---|---|---|---|---|---|---|---|---|---|---|---|---|
| 24A | - | + | | | | | | | | | | | | | | | | | | | | | | | | | | | | | |
| 24B | + | + | + | | | | | | | | | | | | | | | | | | | | | | | | | | | | |
| 24C | | | + | + | | | | | | | | | | | | | | | | | | | | | | | | | | | |
| 24D | | | | - | + | + | + | | | | | | | | | | | | | | | | | | | | | | | | |
| 24E | | | | | | + | - | + | - | + | + | - | + | - | + | - | + | | | | | | | | | | | | | | |
| 24F | | | | | | | | | | | | | | | | | + | + | + | + | | | | | | | | | | | |
| 24G | | | | | | | | | | | | | | | | | | | | - | + | - | + | - | - | + | - | - | + | + | + |
| 24H | | | | | | | | | | | | | | | | | | | | + | | + | | + | + | | | | | - | - |

FIG. 7

| | A | B | C | D | E | F | G | H | I | J | K | L | M | N | O | P | Q | R | S | T | U | V | W |
|---|---|---|---|---|---|---|---|---|---|---|---|---|---|---|---|---|---|---|---|---|---|---|---|
| E0 | - | - | | | | | | + | | | + | | | | | | | | | | | | |
| E1 | + | + | | - | + | + | - | - | | + | - | - | + | + | + | + | | | | | | | |
| E2 | + | + | + | + | + | | | - | - | | | - | - | - | | - | | | | | | | |
| E3 | | + | | | | | | + | + | + | + | + | + | + | + | + | | | | | | | |
| E4 | | | | | | | | | | | | | | | | | + | + | + | + | + | + | + |
| E5 | | | | | | | | | | | | | | | | | + | + | - | - | - | - | - |

FIG. 8

| | A | B | C | D | E | F | G | H | I | J | K | L | M | N | O |
|---|---|---|---|---|---|---|---|---|---|---|---|---|---|---|---|
| E0 | − | − | − |   |   | + | + | + |   |   |   |   |   |   |   |
| E1 | + | + |   | − |   |   | − | − |   |   | + | + | + | + |   |
| E2 |   | + | + | − | − | − |   | − | − | − | − | − |   | + | + |
| E3 |   |   | + | + | + | + |   | + | + | + |   | − | − | − | − |

FIG. 9

| | A | B | C | D | E | F | G | H | I | J | K | L | M | N | O | P | Q | R | S |
|---|---|---|---|---|---|---|---|---|---|---|---|---|---|---|---|---|---|---|---|
| E0 | − | − | − |   |   | + | + | + |   |   |   |   |   |   |   |   |   |   |   |
| E1 | + | + |   | − | − | − |   | − | − | + | + | + |   |   |   |   |   |   |   |
| E2 |   | + | + | + | + | + |   | − | − | − | + | − |   | + | + | + | + | + | + |
| E3 |   |   |   |   |   |   |   | + | + | + |   | − | + | − | − | − | − | + | + |
| E4 |   |   |   |   |   |   |   |   |   |   |   | + | + | + |   |   |   |   | − |

|      |             | Electrode |||||||||
| Step | Electrode Combination | 24A | 24B | 24C | 24D | 24E | 24F | 24G | 24H |
| --- | --- | --- | --- | --- | --- | --- | --- | --- | --- |
| 1 | A | -100% | +100% | | | | | | |
| 2 | B1 | -100% | +90% | +10% | | | | | |
| 3 | B2 | -100% | +80% | +20% | | | | | |
| 4 | B3 | -100% | +70% | +30% | | | | | |
| 5 | B4 | -100% | +60% | +40% | | | | | |
| 6 | B5 | -100% | +50% | +50% | | | | | |
| 7 | B6 | -100% | +40% | +60% | | | | | |
| 8 | B7 | -100% | +30% | +70% | | | | | |
| 9 | B8 | -100% | +20% | +80% | | | | | |
| 10 | B9 | -100% | +10% | +90% | | | | | |
| 11 | C | -100% | | +100% | | | | | |
| 12 | D1 | -90% | -10% | +100% | | | | | |
| 13 | D2 | -80% | -20% | +100% | | | | | |
| 14 | D3 | -70% | -30% | +100% | | | | | |
| 15 | D4 | -60% | -40% | +100% | | | | | |
| 16 | D5 | -50% | -50% | +100% | | | | | |
| 17 | D6 | -40% | -60% | +100% | | | | | |
| 18 | D7 | -30% | -70% | +100% | | | | | |
| 19 | D8 | -20% | -80% | +100% | | | | | |
| 20 | D9 | -10% | -90% | +100% | | | | | |
| 21 | E | | -100% | +100% | | | | | |
| 22 | F1 | +10% | -100% | +90% | | | | | |
| 23 | F2 | +20% | -100% | +80% | | | | | |
| 24 | F3 | +30% | -100% | +70% | | | | | |
| 25 | F4 | +40% | -100% | +60% | | | | | |
| 26 | F5 | +50% | -100% | +50% | | | | | |
| 27 | F6 | +60% | -100% | +40% | | | | | |
| 28 | F7 | +70% | -100% | +30% | | | | | |
| 29 | F8 | +80% | -100% | +20% | | | | | |
| 30 | F9 | +90% | -100% | +10% | | | | | |
| 31 | G | +100% | -100% | | | | | | |
| 32 | H1 | +90% | -90% | -10% | +10% | | | | |
| 33 | H2 | +80% | -80% | -20% | +20% | | | | |
| 34 | H3 | +70% | -70% | -30% | +30% | | | | |
| 35 | H4 | +60% | -60% | -40% | +40% | | | | |
| 36 | H5 | +50% | -50% | -50% | +50% | | | | |
| 37 | H6 | +40% | -40% | -60% | +60% | | | | |
| 38 | H7 | +30% | -30% | -70% | +70% | | | | |
| 39 | H8 | +20% | -20% | -80% | +80% | | | | |
| 40 | H9 | +10% | -10% | -90% | +90% | | | | |

FIG. 10A

| Step | Electrode Combination | Electrode | | | | | | | |
|---|---|---|---|---|---|---|---|---|---|
| | | 24A | 24B | 24C | 24D | 24E | 24F | 24G | 24H |
| 41 | I | | | -100% | +100% | | | | |
| 42 | J1 | | | +10% | -100% | +90% | | | |
| 43 | J2 | | | +20% | -100% | +80% | | | |
| 44 | J3 | | | +30% | -100% | +70% | | | |
| 45 | J4 | | | +40% | -100% | +60% | | | |
| 46 | J5 | | | +50% | -100% | +50% | | | |
| 47 | J6 | | | +60% | -100% | +40% | | | |
| 48 | J7 | | | +70% | -100% | +30% | | | |
| 49 | J8 | | | +80% | -100% | +20% | | | |
| 50 | J9 | | | +90% | -100% | +10% | | | |
| 51 | K | | | +100% | -100% | | | | |
| 52 | L1 | | | +90% | -90% | -10% | +10% | | |
| 53 | L2 | | | +80% | -80% | -20% | +20% | | |
| 54 | L3 | | | +70% | -70% | -30% | +30% | | |
| 55 | L4 | | | +60% | -60% | -40% | +40% | | |
| 56 | L5 | | | +50% | -50% | -50% | +50% | | |
| 57 | L6 | | | +40% | -40% | -60% | +60% | | |
| 58 | L7 | | | +30% | -30% | -70% | +70% | | |
| 59 | L8 | | | +20% | -20% | -80% | +80% | | |
| 60 | L9 | | | +10% | -10% | -90% | +90% | | |
| 61 | M | | | | -100% | +100% | | | |
| 62 | N1 | | | | +10% | -100% | +90% | | |
| 63 | N2 | | | | +20% | -100% | +80% | | |
| 64 | N3 | | | | +30% | -100% | +70% | | |
| 65 | N4 | | | | +40% | -100% | +60% | | |
| 66 | N5 | | | | +50% | -100% | +50% | | |
| 67 | N6 | | | | +60% | -100% | +40% | | |
| 68 | N7 | | | | +70% | -100% | +30% | | |
| 69 | N8 | | | | +80% | -100% | +20% | | |
| 70 | N9 | | | | +90% | -100% | +10% | | |
| 71 | O | | | | +100% | -100% | | | |
| 72 | P1 | | | | +90% | -90% | -10% | +10% | |
| 73 | P2 | | | | +80% | -80% | -20% | +20% | |
| 74 | P3 | | | | +70% | -70% | -30% | +30% | |
| 75 | P4 | | | | +60% | -60% | -40% | +40% | |
| 76 | P5 | | | | +50% | -50% | -50% | +50% | |
| 77 | P6 | | | | +40% | -40% | -60% | +60% | |
| 78 | P7 | | | | +30% | -30% | -70% | +70% | |
| 79 | P8 | | | | +20% | -20% | -80% | +80% | |
| 80 | P9 | | | | +10% | -10% | -90% | +90% | |
| 81 | Q | | | | | -100% | +100% | | |

FIG. 10B

|  |  | Electrode | | | | | | | |
| --- | --- | --- | --- | --- | --- | --- | --- | --- | --- |
| Step | Electrode Combination | 24A | 24B | 24C | 24D | 24E | 24F | 24G | 24H |
| 82 | R1 |  |  |  | + 10% | - 100% | + 90% |  |  |
| 83 | R2 |  |  |  | + 20% | - 100% | + 80% |  |  |
| 84 | R3 |  |  |  | + 30% | - 100% | + 70% |  |  |
| 85 | R4 |  |  |  | + 40% | - 100% | + 60% |  |  |
| 86 | R5 |  |  |  | + 50% | - 100% | + 50% |  |  |
| 87 | R6 |  |  |  | + 60% | - 100% | + 40% |  |  |
| 88 | R7 |  |  |  | + 70% | - 100% | + 30% |  |  |
| 89 | R8 |  |  |  | + 80% | - 100% | + 20% |  |  |
| 90 | R9 |  |  |  | + 90% | - 100% | + 10% |  |  |
| 91 | S |  |  |  | + 100% | - 100% |  |  |  |
| 92 | T1 |  |  |  | + 90% | - 90% | - 10% | + 10% |  |
| 93 | T2 |  |  |  | + 80% | - 80% | - 20% | + 20% |  |
| 94 | T3 |  |  |  | + 70% | - 70% | - 30% | + 30% |  |
| 95 | T4 |  |  |  | + 60% | - 60% | - 40% | + 40% |  |
| 96 | T5 |  |  |  | + 50% | - 50% | - 50% | + 50% |  |
| 97 | T6 |  |  |  | + 40% | - 40% | - 60% | + 60% |  |
| 98 | T7 |  |  |  | + 30% | - 30% | - 70% | + 70% |  |
| 99 | T8 |  |  |  | + 20% | - 20% | - 80% | + 80% |  |
| 100 | T9 |  |  |  | + 10% | - 10% | - 90% | + 90% |  |
| 101 | U |  |  |  |  |  | - 100% | + 100% |  |
| 102 | V1 |  |  |  |  | + 10% | - 100% | + 90% |  |
| 103 | V2 |  |  |  |  | + 20% | - 100% | + 80% |  |
| 104 | V3 |  |  |  |  | + 30% | - 100% | + 70% |  |
| 105 | V4 |  |  |  |  | + 40% | - 100% | + 60% |  |
| 106 | V5 |  |  |  |  | + 50% | - 100% | + 50% |  |
| 107 | V6 |  |  |  |  | + 60% | - 100% | + 40% |  |
| 108 | V7 |  |  |  |  | + 70% | - 100% | + 30% |  |
| 109 | V8 |  |  |  |  | + 80% | - 100% | + 20% |  |
| 110 | V9 |  |  |  |  | + 90% | - 100% | + 10% |  |
| 111 | W |  |  |  |  | + 100% | - 100% |  |  |
| 112 | X1 |  |  |  |  | + 90% | - 90% | - 10% | + 10% |
| 113 | X2 |  |  |  |  | + 80% | - 80% | - 20% | + 20% |
| 114 | X3 |  |  |  |  | + 70% | - 70% | - 30% | + 30% |
| 115 | X4 |  |  |  |  | + 60% | - 60% | - 40% | + 40% |
| 116 | X5 |  |  |  |  | + 50% | - 50% | - 50% | + 50% |
| 117 | X6 |  |  |  |  | + 40% | - 40% | - 60% | + 60% |
| 118 | X7 |  |  |  |  | + 30% | - 30% | - 70% | + 70% |
| 119 | X8 |  |  |  |  | + 20% | - 20% | - 80% | + 80% |
| 120 | X9 |  |  |  |  | + 10% | - 10% | - 90% | + 90% |
| 121 | Y |  |  |  |  |  |  | - 100% | + 100% |
| 122 | Z1 |  |  |  |  |  | + 10% | - 100% | + 90% |

FIG. 10C

| Step | Electrode Combination | Electrode | | | | | | | |
|---|---|---|---|---|---|---|---|---|---|
| | | 24A | 24B | 24C | 24D | 24E | 24F | 24G | 24H |
| 123 | Z2 | | | | | | + 20% | - 100% | + 80% |
| 124 | Z3 | | | | | | + 30% | - 100% | + 70% |
| 125 | Z4 | | | | | | + 40% | - 100% | + 60% |
| 126 | Z5 | | | | | | + 50% | - 100% | + 50% |
| 127 | Z6 | | | | | | + 60% | - 100% | + 40% |
| 128 | Z7 | | | | | | + 70% | - 100% | + 30% |
| 129 | Z8 | | | | | | + 80% | - 100% | + 20% |
| 130 | Z9 | | | | | | + 90% | - 100% | + 10% |
| 131 | AA | | | | | | + 100% | - 100% | |
| 132 | BB1 | | | | | | + 100% | - 90% | - 10% |
| 133 | BB2 | | | | | | + 100% | - 80% | - 20% |
| 134 | BB3 | | | | | | + 100% | - 70% | - 30% |
| 135 | BB4 | | | | | | + 100% | - 60% | - 40% |
| 136 | BB5 | | | | | | + 100% | - 50% | - 50% |
| 137 | BB6 | | | | | | + 100% | - 40% | - 60% |
| 138 | BB7 | | | | | | + 100% | - 30% | - 70% |
| 139 | BB8 | | | | | | + 100% | - 20% | - 80% |
| 140 | BB9 | | | | | | + 100% | - 10% | - 90% |
| 141 | CC | | | | | | + 100% | | - 100% |
| 142 | DD1 | | | | | | + 90% | + 10% | - 100% |
| 143 | DD2 | | | | | | + 80% | + 20% | - 100% |
| 144 | DD3 | | | | | | + 70% | + 30% | - 100% |
| 145 | DD4 | | | | | | + 60% | + 40% | - 100% |
| 146 | DD5 | | | | | | + 50% | + 50% | - 100% |
| 147 | DD6 | | | | | | + 40% | + 60% | - 100% |
| 148 | DD7 | | | | | | + 30% | + 70% | - 100% |
| 149 | DD8 | | | | | | + 20% | + 80% | - 100% |
| 150 | DD9 | | | | | | + 10% | + 90% | - 100% |
| 151 | EE | | | | | | | + 100% | - 100% |

FIG. 10D

|     |                        | Electrode |          |          |        |     |     |     |     |
| --- | ---------------------- | --------- | -------- | -------- | ------ | --- | --- | --- | --- |
| Step | Electrode Combination | 24A       | 24B      | 24C      | 24D    | 24E | 24F | 24G | 24H |
| 1   | A                      | -5.0 mA   | 100%     |          |        |     |     |     |     |
| 2   | B1                     | -5.0 mA   | + 90%    | + 10%    |        |     |     |     |     |
| 3   | B2                     | -5.0 mA   | + 80%    | + 20%    |        |     |     |     |     |
| 4   | B3                     | -5.0 mA   | + 70%    | + 30%    |        |     |     |     |     |
| 5   | B4                     | -5.0 mA   | + 60%    | + 40%    |        |     |     |     |     |
| 6   | B5                     | -5.0 mA   | + 50%    | + 50%    |        |     |     |     |     |
| 7   | B6                     | -5.0 mA   | + 40%    | + 60%    |        |     |     |     |     |
| 8   | B7                     | -5.0 mA   | + 30%    | + 70%    |        |     |     |     |     |
| 9   | B8                     | -5.0 mA   | + 20%    | + 80%    |        |     |     |     |     |
| 10  | B9                     | -5.0 mA   | + 10%    | + 90%    |        |     |     |     |     |
| 11  | C                      | -5.0 mA   |          | + 100%   |        |     |     |     |     |
| 12  | D1                     | -4.5 mA   | -0.5 mA  | + 100%   |        |     |     |     |     |
| 13  | D2                     | -4.0 mA   | -1.0 mA  | + 100%   |        |     |     |     |     |
| 14  | D3                     | -3.5 mA   | -1.5 mA  | + 100%   |        |     |     |     |     |
| 15  | D4                     | -3.0 mA   | -2.0 mA  | + 100%   |        |     |     |     |     |
| 16  | D5                     | -2.5 mA   | -2.5 mA  | + 100%   |        |     |     |     |     |
| 17  | D6                     | -2.0 mA   | -3.0 mA  | + 100%   |        |     |     |     |     |
| 18  | D7                     | -1.5 mA   | -3.5 mA  | + 100%   |        |     |     |     |     |
| 19  | D8                     | -1.0 mA   | -4.0 mA  | + 100%   |        |     |     |     |     |
| 20  | D9                     | -0.5 mA   | -4.5 mA  | + 100%   |        |     |     |     |     |
| 21  | E                      |           | -5.0 mA  | + 100%   |        |     |     |     |     |
| 22  | F1                     | + 10%     | -5.0 mA  | + 90%    |        |     |     |     |     |
| 23  | F2                     | + 20%     | -5.0 mA  | + 80%    |        |     |     |     |     |
| 24  | F3                     | + 30%     | -5.0 mA  | + 70%    |        |     |     |     |     |
| 25  | F4                     | + 40%     | -5.0 mA  | + 60%    |        |     |     |     |     |
| 26  | F5                     | + 50%     | -5.0 mA  | + 50%    |        |     |     |     |     |
| 27  | F6                     | + 60%     | -5.0 mA  | + 40%    |        |     |     |     |     |
| 28  | F7                     | + 70%     | -5.0 mA  | + 30%    |        |     |     |     |     |
| 29  | F8                     | + 80%     | -5.0 mA  | + 20%    |        |     |     |     |     |
| 30  | F9                     | + 90%     | -5.0 mA  | + 10%    |        |     |     |     |     |
| 31  | G                      | + 100%    | -5.0 mA  |          |        |     |     |     |     |
| 32  | H1                     | + 90%     | -4.5 mA  | -0.5 mA  | + 10%  |     |     |     |     |
| 33  | H2                     | + 80%     | -4.0 mA  | -1.0 mA  | + 20%  |     |     |     |     |
| 34  | H3                     | + 70%     | -3.5 mA  | -1.5 mA  | + 30%  |     |     |     |     |
| 35  | H4                     | + 60%     | -3.0 mA  | -2.0 mA  | + 40%  |     |     |     |     |
| 36  | H5                     | + 50%     | -2.5 mA  | -2.5 mA  | + 50%  |     |     |     |     |
| 37  | H6                     | + 40%     | -2.0 mA  | -3.0 mA  | + 60%  |     |     |     |     |
| 38  | H7                     | + 30%     | -1.5 mA  | -3.5 mA  | + 70%  |     |     |     |     |
| 39  | H8                     | + 20%     | -1.0 mA  | -4.0 mA  | + 80%  |     |     |     |     |
| 40  | H9                     | + 10%     | -0.5 mA  | -4.5 mA  | + 90%  |     |     |     |     |
| 41  | I                      |           |          | -5.0 mA  | + 100% |     |     |     |     |

FIG. 11A

| Step | Electrode Combination | Electrode | | | | | | | |
|---|---|---|---|---|---|---|---|---|---|
| | | 24A | 24B | 24C | 24D | 24E | 24F | 24G | 24H |
| 42 | J1 | | + 10% | -5.0 mA | + 90% | | | | |
| 43 | J2 | | + 20% | -5.0 mA | + 80% | | | | |
| 44 | J3 | | + 30% | -5.0 mA | + 70% | | | | |
| 45 | J4 | | + 40% | -5.0 mA | + 60% | | | | |
| 46 | J5 | | + 50% | -5.0 mA | + 50% | | | | |
| 47 | J6 | | + 60% | -5.0 mA | + 40% | | | | |
| 48 | J7 | | + 70% | -5.0 mA | + 30% | | | | |
| 49 | J8 | | + 80% | -5.0 mA | + 20% | | | | |
| 50 | J9 | | + 90% | -5.0 mA | + 10% | | | | |
| 51 | K | | + 100% | -5.0 mA | | | | | |
| 52 | L1 | | + 90% | -4.5 mA | -0.5 mA | + 10% | | | |
| 53 | L2 | | + 80% | -4.0 mA | -1.0 mA | + 20% | | | |
| 54 | L3 | | + 70% | -3.5 mA | -1.5 mA | + 30% | | | |
| 55 | L4 | | + 60% | -3.0 mA | -2.0 mA | + 40% | | | |
| 56 | L5 | | + 50% | -2.5 mA | -2.5 mA | + 50% | | | |
| 57 | L6 | | + 40% | -2.0 mA | -3.0 mA | + 60% | | | |
| 58 | L7 | | + 30% | -1.5 mA | -3.5 mA | + 70% | | | |
| 59 | L8 | | + 20% | -1.0 mA | -4.0 mA | + 80% | | | |
| 60 | L9 | | + 10% | -0.5 mA | -4.5 mA | + 90% | | | |
| 61 | M | | | | -5.0 mA | + 100% | | | |
| 62 | N1 | | | + 10% | -5.0 mA | + 90% | | | |
| 63 | N2 | | | + 20% | -5.0 mA | + 80% | | | |
| 64 | N3 | | | + 30% | -5.0 mA | + 70% | | | |
| 65 | N4 | | | + 40% | -5.0 mA | + 60% | | | |
| 66 | N5 | | | + 50% | -5.0 mA | + 50% | | | |
| 67 | N6 | | | + 60% | -5.0 mA | + 40% | | | |
| 68 | N7 | | | + 70% | -5.0 mA | + 30% | | | |
| 69 | N8 | | | + 80% | -5.0 mA | + 20% | | | |
| 70 | N9 | | | + 90% | -5.0 mA | + 10% | | | |
| 71 | O | | | + 100% | -5.0 mA | | | | |
| 72 | P1 | | | + 90% | -4.5 mA | -0.5 mA | + 10% | | |
| 73 | P2 | | | + 80% | -4.0 mA | -1.0 mA | + 20% | | |
| 74 | P3 | | | + 70% | -3.5 mA | -1.5 mA | + 30% | | |
| 75 | P4 | | | + 60% | -3.0 mA | -2.0 mA | + 40% | | |
| 76 | P5 | | | + 50% | -2.5 mA | -2.5 mA | + 50% | | |
| 77 | P6 | | | + 40% | -2.0 mA | -3.0 mA | + 60% | | |
| 78 | P7 | | | + 30% | -1.5 mA | -3.5 mA | + 70% | | |
| 79 | P8 | | | + 20% | -1.0 mA | -4.0 mA | + 80% | | |
| 80 | P9 | | | + 10% | -0.5 mA | -4.5 mA | + 90% | | |
| 81 | Q | | | | | -5.0 mA | + 100% | | |
| 82 | R1 | | | | + 10% | -5.0 mA | + 90% | | |
| 83 | R2 | | | | + 20% | -5.0 mA | + 80% | | |

FIG. 11B

|      |                        | Electrode |     |     |       |         |         |       |     |
|------|------------------------|-----------|-----|-----|-------|---------|---------|-------|-----|
| Step | Electrode Combination  | 24A       | 24B | 24C | 24D   | 24E     | 24F     | 24G   | 24H |
| 84   | R3                     |           |     |     | +30%  | -5.0 mA | +70%    |       |     |
| 85   | R4                     |           |     |     | +40%  | -5.0 mA | +60%    |       |     |
| 86   | R5                     |           |     |     | +50%  | -5.0 mA | +50%    |       |     |
| 87   | R6                     |           |     |     | +60%  | -5.0 mA | +40%    |       |     |
| 88   | R7                     |           |     |     | +70%  | -5.0 mA | +30%    |       |     |
| 89   | R8                     |           |     |     | +80%  | -5.0 mA | +20%    |       |     |
| 90   | R9                     |           |     |     | +90%  | -5.0 mA | +10%    |       |     |
| 91   | S                      |           |     |     | +100% | -5.0 mA |         |       |     |
| 92   | T1                     |           |     |     | +90%  | -4.5 mA | -0.5 mA | +10%  |     |
| 93   | T2                     |           |     |     | +80%  | -4.0 mA | -1.0 mA | +20%  |     |
| 94   | T3                     |           |     |     | +70%  | -3.5 mA | -1.5 mA | +30%  |     |
| 95   | T4                     |           |     |     | +60%  | -3.0 mA | -2.0 mA | +40%  |     |
| 96   | T5                     |           |     |     | +50%  | -2.5 mA | -2.5 mA | +50%  |     |
| 97   | T6                     |           |     |     | +40%  | -2.0 mA | -3.0 mA | +60%  |     |
| 98   | T7                     |           |     |     | +30%  | -1.5 mA | -3.5 mA | +70%  |     |
| 99   | T8                     |           |     |     | +20%  | -1.0 mA | -4.0 mA | +80%  |     |
| 100  | T9                     |           |     |     | +10%  | -0.5 mA | -4.5 mA | +90%  |     |
| 101  | U                      |           |     |     |       |         | -5.0 mA | +100% |     |
| 102  | V1                     |           |     |     |       | +10%    | -5.0 mA | +90%  |     |
| 103  | V2                     |           |     |     |       | +20%    | -5.0 mA | +80%  |     |
| 104  | V3                     |           |     |     |       | +30%    | -5.0 mA | +70%  |     |
| 105  | V4                     |           |     |     |       | +40%    | -5.0 mA | +60%  |     |
| 106  | V5                     |           |     |     |       | +50%    | -5.0 mA | +50%  |     |
| 107  | V6                     |           |     |     |       | +60%    | -5.0 mA | +40%  |     |
| 108  | V7                     |           |     |     |       | +70%    | -5.0 mA | +30%  |     |
| 109  | V8                     |           |     |     |       | +80%    | -5.0 mA | +20%  |     |
| 110  | V9                     |           |     |     |       | +90%    | -5.0 mA | +10%  |     |
| 111  | W                      |           |     |     |       | +100%   | -5.0 mA |       |     |
| 112  | X1                     |           |     |     |       | +90%    | -4.5 mA | -0.5 mA | +10% |
| 113  | X2                     |           |     |     |       | +80%    | -4.0 mA | -1.0 mA | +20% |
| 114  | X3                     |           |     |     |       | +70%    | -3.5 mA | -1.5 mA | +30% |
| 115  | X4                     |           |     |     |       | +60%    | -3.0 mA | -2.0 mA | +40% |
| 116  | X5                     |           |     |     |       | +50%    | -2.5 mA | -2.5 mA | +50% |
| 117  | X6                     |           |     |     |       | +40%    | -2.0 mA | -3.0 mA | +60% |
| 118  | X7                     |           |     |     |       | +30%    | -1.5 mA | -3.5 mA | +70% |
| 119  | X8                     |           |     |     |       | +20%    | -1.0 mA | -4.0 mA | +80% |
| 120  | X9                     |           |     |     |       | +10%    | -0.5 mA | -4.5 mA | +90% |
| 121  | Y                      |           |     |     |       |         |         | -5.0 mA | +100% |
| 122  | Z1                     |           |     |     |       |         | +10%    | -5.0 mA | +90% |
| 123  | Z2                     |           |     |     |       |         | +20%    | -5.0 mA | +80% |
| 124  | Z3                     |           |     |     |       |         | +30%    | -5.0 mA | +70% |
| 125  | Z4                     |           |     |     |       |         | +40%    | -5.0 mA | +60% |

FIG. 11C

|      |             | Electrode |     |     |     |     |        |         |         |
|------|-------------|-----------|-----|-----|-----|-----|--------|---------|---------|
| Step | Electrode Combination | 24A | 24B | 24C | 24D | 24E | 24F | 24G | 24H |
| 126  | Z5          |           |     |     |     |     | +50%   | -5.0 mA | +50%    |
| 127  | Z6          |           |     |     |     |     | +60%   | -5.0 mA | +40%    |
| 128  | Z7          |           |     |     |     |     | +70%   | -5.0 mA | +30%    |
| 129  | Z8          |           |     |     |     |     | +80%   | -5.0 mA | +20%    |
| 130  | Z9          |           |     |     |     |     | +90%   | -5.0 mA | +10%    |
| 131  | AA          |           |     |     |     |     | +100%  | -5.0 mA |         |
| 132  | BB1         |           |     |     |     |     | +100%  | -4.5 mA | -0.5 mA |
| 133  | BB2         |           |     |     |     |     | +100%  | -4.0 mA | -1.0 mA |
| 134  | BB3         |           |     |     |     |     | +100%  | -3.5 mA | -1.5 mA |
| 135  | BB4         |           |     |     |     |     | +100%  | -3.0 mA | -2.0 mA |
| 136  | BB5         |           |     |     |     |     | +100%  | -2.5 mA | -2.5 mA |
| 137  | BB6         |           |     |     |     |     | +100%  | -2.0 mA | -3.0 mA |
| 138  | BB7         |           |     |     |     |     | +100%  | -1.5 mA | -3.5 mA |
| 139  | BB8         |           |     |     |     |     | +100%  | -1.0 mA | -4.0 mA |
| 140  | BB9         |           |     |     |     |     | +100%  | -0.5 mA | -4.5 mA |
| 141  | CC          |           |     |     |     |     | +100%  |         | -5.0 mA |
| 142  | DD1         |           |     |     |     |     | +90%   | +10%    | -5.0 mA |
| 143  | DD2         |           |     |     |     |     | +80%   | +20%    | -5.0 mA |
| 144  | DD3         |           |     |     |     |     | +70%   | +30%    | -5.0 mA |
| 145  | DD4         |           |     |     |     |     | +60%   | +40%    | -5.0 mA |
| 146  | DD5         |           |     |     |     |     | +50%   | +50%    | -5.0 mA |
| 147  | DD6         |           |     |     |     |     | +40%   | +60%    | -5.0 mA |
| 148  | DD7         |           |     |     |     |     | +30%   | +70%    | -5.0 mA |
| 149  | DD8         |           |     |     |     |     | +20%   | +80%    | -5.0 mA |
| 150  | DD9         |           |     |     |     |     | +10%   | +90%    | -5.0 mA |
| 151  | EE          |           |     |     |     |     |        | +100%   | -5.0 mA |

FIG. 11D

IDENTIFICATION OF ELECTRODE COMBINATION FOR EFFICACIOUS ELECTRICAL STIMULATION THERAPY

This application is a continuation of U.S. application Ser. No. 13/796,529 by Torgerson et al., which was filed on Mar. 12, 2013 and is entitled, "IDENTIFICATION OF ELECTRODE COMBINATION FOR EFFICACIOUS ELECTRICAL STIMULATION THERAPY." The entire content of U.S. application Ser. No. 13/796,529, which issued as U.S. Pat. No. 8,918,184 on Dec. 23, 2014, is incorporated herein by reference.

TECHNICAL FIELD

The disclosure relates to therapy delivery by a medical device and, more particularly, delivery of electrical stimulation therapy.

BACKGROUND

Medical devices, such as electrical stimulators, may be used in different therapeutic applications, such as deep brain stimulation (DBS), spinal cord stimulation (SCS), pelvic stimulation, gastric stimulation, peripheral nerve stimulation, functional electrical stimulation. A medical device may be configured to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastroparesis or diabetes. In some therapy systems, an or external electrical stimulator delivers electrical therapy to a target tissue site within a patient with the aid of one or more electrodes, which may be deployed by medical leads.

During a programming session, a clinician may select one or more therapy programs (which may also referred to as therapy parameter sets) that provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered and the electrode combination with which the electrical stimulation is delivered. In examples in which electrical stimulation is delivered in the form of electrical pulses, for example, the therapy parameters may include an electrode combination, an amplitude, which may be a current or voltage amplitude, a pulse width, and a pulse rate.

SUMMARY

The disclosure describes devices, systems, and techniques for identifying one or more electrode combinations for delivering electrical stimulation therapy to a patient. In some examples, electrode combinations of a predefined set of electrode combinations are automatically tested for delivery of electrical stimulation therapy to a patient in a predetermined order, where the electrode combinations are arranged in the predetermined order such that adjacent electrode combinations in the order include at least one shared anode electrode or cathode electrode. In addition, in some examples, the electrode combinations of the set are arranged in the predetermined order such that electrode combinations propagate down the lead (e.g., from a proximal end of the lead to a distal end of the lead or vice versa) as electrode combinations are tested in the predetermined order.

In some examples, the set of electrode combinations tested in the predetermined order define a predetermined sequence of electrode patterns, each electrode pattern defining a relative arrangement between one or more anodes and one or more cathodes of the respective electrode pattern. An electrode combination may be defined by a subset of electrodes of a lead with which electrical stimulation is delivered to the patient, and the polarities of the particular electrodes. Thus, the electrode combination may be defined by a subset of electrodes of a lead, respective electrode polarities, and an electrode pattern.

In some examples, the electrode patterns are selected such that the anode and cathode electrodes of every electrode combination in the predefined set are programmed together on adjacent electrodes without any inactive (also referred to as "off" or "unused") electrodes between the active electrodes. This type of arrangement of anode and cathode electrodes may minimize the area of activation of the neurons as the electrode combinations propagate down the electrode array, and provide more precise electrical stimulation.

In some examples, at least one electrode pattern may appear multiple times at different positions in the predetermined sequence. For example, the predetermined sequence may include a repeating sequence of electrode patterns. The sequence of electrode patterns may be repeated as, for example, electrode combinations are propagated down a lead.

In some examples, the amplitudes assigned to the anode and cathode electrodes of test electrode combinations, referred to herein as anodic amplitudes and cathodic amplitudes, respectively, are adjusted in a predetermined manner as the electrode combinations of the predefined set are tested in the predetermined order. The predetermined manner may be selected such that one or more electrode combinations of the predefined set are delivered with different combinations of anodic and cathodic amplitudes. For example, the anodic amplitude and/or cathodic amplitudes may be incrementally modified (e.g., increased or decreased) in the predetermined manner, according to a predefined schedule, during the automatic delivery of electrical stimulation via the predefined set of electrode combinations. For a particular electrode combination, the efficacy of therapy may change depending on the anodic amplitude, cathodic amplitude, or both, of each of the active anodes and cathodes, respectively. Thus, automatically adjusting the anodic amplitude and/or cathodic amplitudes in a predetermined manner may help thoroughly test one or more electrode combinations in an efficient manner.

In addition, the incremental modification to the anodic amplitude and/or cathodic amplitude may result in transitions between electrode combinations that may minimize discomfort to the patient and minimize, if not eliminate, user input required to manually adjust the amplitudes.

In one aspect, the disclosure is directed to a method comprising, with one or more processors, selecting a predefined set of electrode combinations, and, with the one or more processors, controlling a medical device to deliver electrical stimulation to a patient via the predefined set of electrode combinations in a predetermined order. The electrode combinations are arranged in the predetermined order such that adjacent electrode combinations in the order include at least one shared anode electrode or cathode electrode. In addition, the electrode combinations in the predetermined order define a predetermined sequence of electrode patterns, each electrode pattern defining a relative arrangement between one or more anodes and one or more cathodes of the respective electrode pattern, where at least one electrode pattern appears multiple times at different positions in the sequence.

In another aspect, the disclosure is directed to a system comprising a medical device and a processor configured to control the medical device to deliver electrical stimulation to a patient via a predefined set of electrode combinations in a predetermined order. The electrode combinations are arranged in the predetermined order such that adjacent electrode combinations in the order include at least one shared anode electrode or cathode electrode. In addition, the electrode combinations in the predetermined order define a predetermined sequence of electrode patterns, each electrode pattern defining a relative arrangement between one or more anodes and one or more cathodes of the respective electrode pattern, where at least one electrode pattern appears multiple times at different positions in the sequence.

In another aspect, the disclosure is directed to a system comprising means for delivering electrical stimulation to a patient, and means for controlling the means for delivering electrical stimulation to deliver electrical stimulation to the patient via a predefined set of electrode combinations in a predetermined order. The electrode combinations are arranged in the predetermined order such that adjacent electrode combinations in the order include at least one shared anode electrode or cathode electrode. In addition, the electrode combinations in the predetermined order define a predetermined sequence of electrode patterns, each electrode pattern defining a relative arrangement between one or more anodes and one or more cathodes of the respective electrode pattern, where at least one electrode pattern appears multiple times at different positions in the sequence.

In another aspect, the disclosure is directed to a computer-readable storage medium comprising instructions. The instructions cause a programmable processor to control a medical device to deliver electrical stimulation to the patient via a predefined set of electrode combinations in a predetermined order and select an electrode combination from the predefined set based on the delivery of the electrical stimulation by the medical device. The electrode combinations are arranged in the predetermined order such that adjacent electrode combinations in the order include at least one shared anode electrode or cathode electrode. In addition, the electrode combinations in the predetermined order define a predetermined sequence of electrode patterns, each electrode pattern defining a relative arrangement between one or more anodes and one or more cathodes of the respective electrode pattern. At least one electrode pattern appears multiple times at different positions in the sequence.

In another aspect, the disclosure is directed to a computer-readable storage medium, which may be an article of manufacture. The computer-readable storage medium includes computer-readable instructions for execution by a processor. The instructions cause a programmable processor to perform any part of the techniques described herein. The instructions may be, for example, software instructions, such as those used to define a software or computer program. The software or computer program may be, for example, modified or otherwise updated base on a specific patient's requirements.

The details of one or more examples are set forth in the accompanying drawings and the description below. Other features, objects, and advantages will be apparent from the description and drawings, and from the claims.

BRIEF DESCRIPTION OF DRAWINGS

FIGS. 6-9 are tables illustrating example sets of test electrode combinations that may be used to identify one or more efficacious electrode combinations for a patient.

FIGS. 10A-10D illustrate an example predefined schedule of amplitude adjustments, which includes an example set of test electrode combinations and corresponding anodic and cathodic amplitudes.

FIGS. 11A-11D illustrate another example predefined schedule of amplitude adjustments.

DETAILED DESCRIPTION

Figure 1:
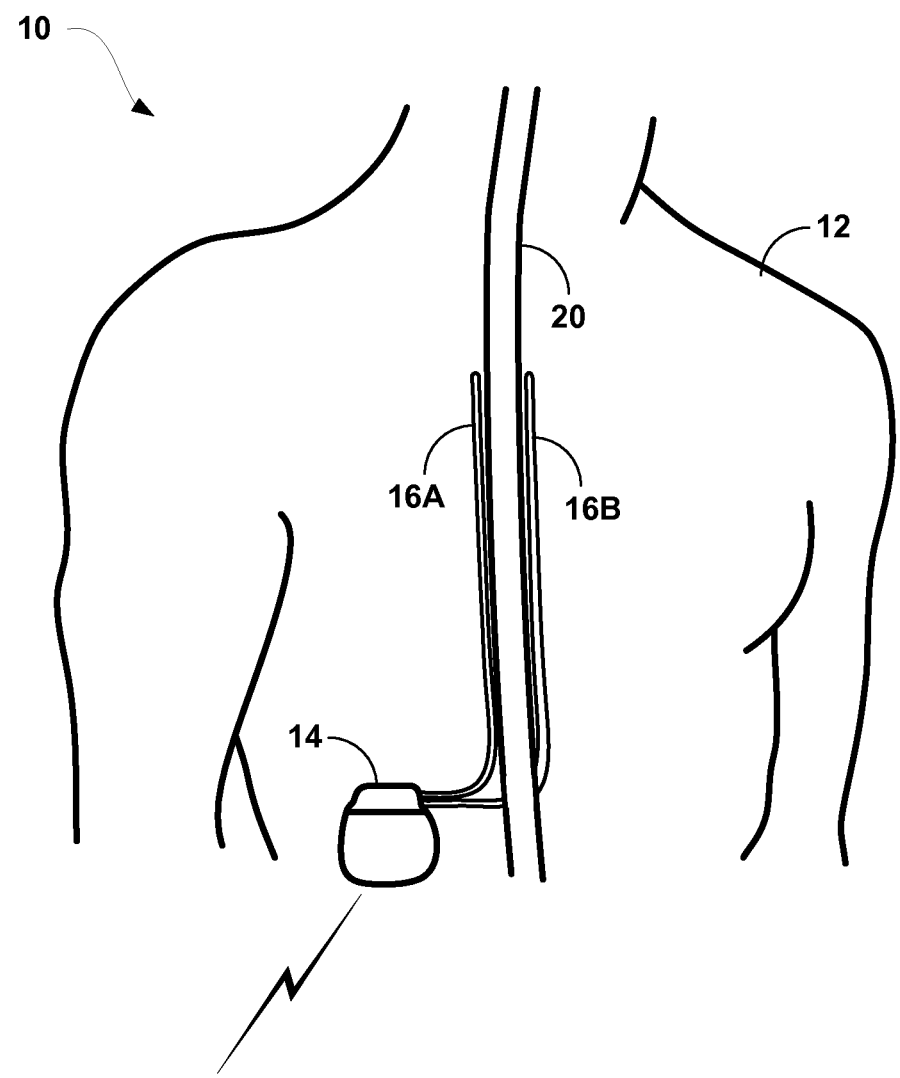
FIG. 1 is a schematic diagram illustrating an example system including a medical device, electrical stimulation leads, and a medical device programmer.

FIG. 1 is a schematic diagram illustrating an example system 10, which is configured to deliver electrical stimulation therapy to patient 12, who is ordinarily a human patient. System 10 includes implantable medical device (IMD) 14 and electrical stimulation leads 16A, 16B (collectively referred to as "electrical stimulation leads 16" or "leads 16"), and external programmer 18. Although the techniques described in this disclosure may be generally applicable to a variety of medical devices including external and implantable medical devices, application of such techniques to implantable medical devices and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices and target therapy delivery sites. For example, in other examples, instead of, or in addition to IMD 14, system 10 may include an external medical device (e.g., an external electrical stimulator) that is not implanted in the patient's body, and percutaneously implanted leads or external leads.

IMD 14 is configured to generate and deliver electrical stimulation therapy to patient 12. IMD 14 may include a biocompatible outer housing, such as titanium or stainless steel, or a polymeric material such as silicone or polyurethane. In examples in which IMD 14 is implanted in patient 12, IMD 14 may be implanted at any suitable location within patient 12.

In the example of FIG. 1, IMD 14 is an implantable electrical stimulator configured for SCS, e.g., for relief of chronic pain or other symptoms. Stimulation energy is delivered from IMD 14 to spinal cord 20 of patient 12 via one or more electrodes of implantable leads 16. In some applications, such as SCS, leads 16 may be implanted in patient 12 such that longitudinal axes of leads 16 (e.g., extending from a proximal end to a distal end of the respective lead) are substantially parallel to one another.

However, other relative arrangements of lead 16 may also be used and may differ depending on the target tissue site for the electrical stimulation therapy. In addition, although two leads 16 are shown in the example shown in FIG. 1, in other examples, system 10 may include any suitable number of leads, such as one lead, three leads, or more than three leads. In addition, in some examples, system 10 may include a leadless electrical stimulator, as discussed in further detail below, Although SCS therapy is primarily referred to throughout the description of FIG. 1, system 10 may be configured to deliver electrical stimulation therapy to patient 12 for any patient condition that may benefit from stimulation therapy. For example, system 10 may be configured to deliver electrical stimulation therapy for treatment of movement disorders or other neurodegenerative impairment, whether by disease or trauma (e.g., disorders with one or more symptoms that affect muscle control and movement problems, such as rigidity, bradykinesia, rhythmic hyperkinesia, nonrhythmic hyperkinesia or akinesia). As another example, system 10 may be configured to deliver electrical stimulation therapy for treatment of Parkinson's disease, seizure disorder (e.g., epilepsy), urinary or fecal incontinence, sexual dysfunction, obesity, gastroparesis, psychiatric disorders (e.g., depression, mania, obsessive compulsive disorder, anxiety disorders, and the like), muscle stimulation (e.g., functional electrical stimulation (FES) of muscles) or obesity. In this manner, in some examples, system 10 may be configured to provide therapy taking the form of any one or more of deep brain stimulation (DBS), peripheral nerve stimulation (PNS), peripheral nerve field stimulation (PNFS), DBS, cortical stimulation (CS), pelvic floor stimulation, gastric stimulation, or any other electrical stimulation therapy.

Leads 16 may be implanted within patient 12 and directly or indirectly (e.g., via a lead extension) electrically connected to IMD 14. As mentioned above, in some other examples, leads 16 may be implanted and coupled to an external stimulator, e.g., through a percutaneous port. The external stimulator may be, for example, a trial or screening stimulation that is used on a temporary basis to evaluate potential efficacy to aid in consideration of chronic implantation for patient 12. In other examples, IMD 14 is a leadless stimulator with one or more arrays of electrodes arranged on a housing of the stimulator in addition to, or instead of, leads 16 that extend from the outer housing of IMD 14.

Leads 16 each include a plurality of electrodes (not shown in FIG. 1) disposed proximate to a distal end of the respective lead and/or at other positions at intermediate points along the lead. Electrodes of leads 16 are configured to deliver electrical stimulation generated by IMD 14 to a target tissue site of patient 12. A selected subset of the electrodes located on leads 16 and the polarities of the electrodes of the subset collectively define an "electrode combination." An electrode combination refers to the combination of single or multiple cathode electrodes and single or multiple anode electrodes with which IMD 14 delivers electrical stimulation signals to patient 12. Stimulation current generated by IMD 14 flows between the cathodes and anodes for delivery of electrical therapy. For example, electrons may flow from the one or more electrodes acting as anodes for an electrode combination to the one or more electrodes acting as cathodes for the combination. The current between cathodes and anodes may stimulate neurons between and proximate to the anodes and the cathodes.

The electrodes of leads 16 may be electrode pads on a paddle lead, circular (e.g., ring) electrodes surrounding the body of the respective lead 16A or 16B, conformable electrodes, cuff electrodes, segmented electrodes, or any other type of electrodes capable of forming unipolar, bipolar or multipolar electrode combinations for therapy. In general, ring electrodes arranged at different axial positions at the distal ends of leads 16 will be described for purposes of illustration.

Leads 16 may be percutaneously or surgically implanted in patient 12 on a temporary or permanent basis such that at least one electrode is positioned proximate to a target tissue site, which may be any tissue affected by electrical stimulation energy. The target tissue site may be, for example, a nerve or other tissue site, such as a spinal cord 20 in the example shown in FIG. 1 (e.g., within an intrathecal space or epidural space of spinal cord 20, or, in some examples, adjacent nerves that branch off of spinal cord 20), a pelvic nerve, a pudendal nerve, a stomach, a bladder, or a brain or other organ of a patient, or a muscle or muscle group of a patient.

In the example shown in FIG. 1, leads 16 may be introduced into spinal cord 20 via any suitable region, such as the thoracic, cervical or lumbar regions. Stimulation of spinal cord 20 may, for example, prevent pain signals from traveling through spinal cord 20 and to the brain of patient 12. Patient 12 may perceive the interruption of pain signals as a reduction in pain and, therefore, efficacious therapy results.

The deployment of electrodes via leads 16 connected to IMD 14 is described for purposes of illustration; an array of electrodes may also be deployed in different ways. For example, a housing associated with a leadless stimulator may carry an array of electrodes, e.g., electrodes arranged to define a plurality of rows and/or columns (or other patterns). Such electrodes may be arranged as surface electrodes, ring electrodes, or protrusions. As another example, an electrode array may be formed by rows and/or columns of electrodes on one or more paddle leads. In some examples, electrode arrays may include electrode segments, which may be arranged at respective positions around a periphery of a lead, e.g., arranged in the form of one or more segmented rings around an outer perimeter of a cylindrical lead. The techniques described herein for identifying one or more efficacious electrode combinations may be used with any array of electrodes.

IMD 14 is configured to generate and deliver electrical stimulation therapy to patient 12 according to a therapy program, which may also be referred to as a set of electrical stimulation parameter values. Delivery of stimulation pulses will be described for purposes of illustration. However, electrical stimulation may be delivered in other forms, such as continuous waveforms. The electrical stimulation may be delivered as controlled voltage pulses or waveforms, or as controlled current pulses or waveforms.

A therapy program defines values for one or more electrical stimulation parameter parameters that define an aspect of the therapy delivered by IMD 14 according to that program. The electrical stimulation parameters may include an electrode combination, voltage or current amplitude of an electrical stimulation signal, a frequency of the electrical stimulation signal, and, in the case of electrical stimulation pulses, pulse rate, pulse width, and other appropriate parameters such as duration or duty cycle. The electrode combination may determine the target tissue site for the electrical stimulation energy, and, therefore, which physiological effects are perceived by patient 12. The intensity and the extent of those effects may be a function of the stimulation rate, pulse width, voltage or current amplitude, or any combination thereof.

In some examples, system 10 stores a plurality of therapy programs (e.g., in a memory of IMD 14, programmer 18 or another device), and IMD 14 is configured to generate and deliver electrical stimulation therapy to patient 12 in accordance with one or more stored therapy programs. In some examples, IMD 14 delivers therapy to patient 12 according to multiple programs, wherein multiple programs are contained within each of a plurality of groups. For example, each program group may support an alternative therapy selectable by patient 12, and IMD 14 may deliver therapy according to the multiple programs by, e.g., rotating through the multiple programs of the group when delivering stimulation such that numerous conditions of patient 12 are treated.

The process of selecting values for the electrical stimulation parameters that provide efficacious results for a particular patient 12 can be time consuming, and may require a great deal of trial and error before a "best" set of therapy parameter values is determined. The "best" set of therapy parameter values may be a set of therapy parameter values that is better than other sets of therapy parameter values tested in terms of clinical efficacy (e.g., symptom relief, coverage area) versus side effects experienced, and, in some cases, based on medical device performance characteristics (e.g., power consumption). During a programming session (or at another time), a clinician may selectively test a relatively large number of electrode combinations in order to identify an efficacious electrode combination. A programming session may occur during implant of IMD 14, during a trial session, during an in-clinic or remote follow-up session after IMD 14 is implanted or otherwise provided to patient 14, or at another time, The process of selecting electrode combinations, e.g., selecting electrodes of leads 16 and the polarities of the electrodes, can be particularly time-consuming and tedious due to the relatively large number of electrode combinations that may be possible from electrodes of leads 16.

During a programming session (or at another time), a clinician may test a plurality of different electrode combinations on patient 12 to identify one or more efficacious electrode combinations, which may then be selected for further testing on patient 12 or for chronic therapy delivery to patient 12, and/or may be used to find additional efficacious electrode combinations. For example, the clinician may control IMD 14 (e.g., via programmer 18) to deliver test (or "trial") electrical stimulation to patient via each of the electrode combinations of the plurality for a respective test period, determine the efficacy of therapy delivered via each of the tested electrode combinations, and select one or more electrode combinations based on the determined efficacy of the tested electrode combinations. The plurality of electrical combinations may tested in real time, e.g., at the clinician's office, during one programming session.

In some existing techniques, a clinician may test electrode combinations by manually specifying each electrode combination to test based on intuition or some idiosyncratic methodology, and recording notes on the efficacy and side effects of each electrode combination after delivery of stimulation via that electrode combination. The clinician may then later compare and select from the tested electrode combinations. As an example illustrating the magnitude of such a task, if two leads 16 include eight electrodes each, then over forty-two million potential electrode combinations are available for testing on patient 12 in order to identify an efficacious electrode combination. While the existing techniques for selecting one or more efficacious electrode combinations may be useful, the existing techniques may also be relatively time consuming. In addition, a lack of a systematic technique for testing different electrode combinations may leave the clinician or patient 12 with a lack of confidence in the selected one or more electrode combinations, e.g., because of a feeling that the "best" electrode combination was not identified.

Devices, systems, and techniques for efficiently identifying one or more electrode combinations for delivering efficacious electrical stimulation therapy to a patient are described herein. The devices, systems, and techniques described herein may enable a clinician or patient 12 to more quickly identify efficacious electrode combinations with which IMD 14 may deliver electrical stimulation therapy to patient 12 compared to the techniques in which a clinician manually selects each test electrode combination.

For ease of description, the techniques are primarily described as being employed by programmer 18. In other examples, the techniques may be implemented by any suitable device, such as IMD 14 or another computing device (e.g., a remote computing device such as a cloud computing device), alone or in combination with programmer 18. In addition, for ease of description, the techniques are primarily described as being employed to select one or more electrode combinations that include a column of electrodes of only lead 16A. In other examples, the techniques may be implemented to select more electrode combinations that include electrodes of only lead 16B, electrodes of both leads 16, and electrodes of a lead including a plurality of columns of electrodes (e.g., a lead including segmented electrodes or a multi-column paddle lead).

In the example shown in FIG. 1, programmer 18 is configured to automatically control IMD 14 to deliver electrical stimulation to patient 12 via each electrode combination of a predefined set of electrode combinations in a predetermined order, and one or more efficacious electrode combinations with which IMD 14 may deliver electrical stimulation therapy to patient 12 can be selected based on the electrical stimulation. For example, programmer 18 may store the predefined set of a plurality of different electrode combinations, and may be configured to automatically select electrode combinations from the set (e.g., with no user intervention selecting electrode combinations) to test on patient 12 in a predetermined order (e.g., a nonrandom order). In this way, programmer 18 may be configured to control IMD 14 to automatically scan through each of the electrode combinations in the predefined set.

In some examples, programmer 18 is configured to automatically scan through each of the electrode combination in the predefined set with limited user interaction. For example, programmer 18 can be configured to start the automatic testing of a predefined set of electrode combinations in response to user input requesting a start the automatic scanning, and to stop the automatic testing in response to user input requesting a stop the automatic scanning. After the scan is started in response to user input, programmer 18 may be configured to automatically (e.g., without user input) select electrode combinations from the predefined set in a predetermined order, and control IMD 14 to deliver electrical stimulation according to the selected electrode combinations in the predetermined order. In contrast to systems in which user interaction is required during a programming session to select electrode combinations to test (e.g., to select a next electrode combination to test after testing a currently selected electrode combination) on patient 12, programmer 18 may be configured to save time and reduce the burden for the user to test a plurality of electrode combinations on patient 12.

In some examples, the electrode combinations of the predefined set may be selected and stored as part of the set prior to initiating the scan (also referred to herein as a propagation) through the electrode combinations of the predefined set. Accordingly, in some examples, a clinician may know which electrode combinations are going to be tested on patient 12 prior to initiating the scan through the electrode combinations of the predefined set. Because IMD 14 delivers the electrical stimulation to identify an efficacious electrode combination, the electrical stimulation delivered during the scanning through the set of electrode combinations may be referred to as "trial" or "test" electrical stimulation. The one or more electrode combinations selected from the set may be used for one or more purposes, such as for further testing on patient 12, generation of one or more therapy programs used for therapy delivery by IMD 14, or for identification of additional electrode combinations to test on patient 12.

In some examples, once the testing of a predefined set of test electrode combinations is initiated, programmer 18 can automatically select the test electrode combinations from the set based on the predetermined order, and control IMD 14 to deliver electrical stimulation via each selected test electrode combination without user intervention, e.g., user input selecting specific electrode combinations to test or indicating a direction in which the electrical stimulation should be shifted. In this way, programmer 18 can be configured to execute an auto-scan of a plurality of electrode combinations on patient 12 that can be run independently of any user control. This may help minimize the amount of clinician knowledge, experience, skill, or any combination thereof, required to identify an efficacious electrode combination for patient 12. Delivery of electrical stimulation by IMD 14 may, but need not be, stopped between test electrode combinations of the set for user parameter adjustments, e.g., to increase or decrease the amplitude of the electrical stimulation.

The predetermined order of the electrode combinations of the set is selected such that the transitions between electrode combinations are logical and efficient, e.g., selected to reduce the amount of time consumed for the transitions. For example, in some examples, the electrode combinations are arranged in the predetermined order such that each electrode combination includes at least one anode or cathode from a preceding electrode combination in the predetermined order. That is, the electrode combinations of the set tested on patient 12 may be arranged in the predetermined order such that adjacent electrode combinations in the order include at least one shared anode electrode or cathode electrode, such as at least one shared anode electrode and at least one shared cathode electrode. This arrangement may help increase the speed with which the plurality of electrode combinations are tested on patient 12, e.g., by reducing the amount of time consumed to increase or decrease the intensity of electrical stimulation delivered via a particular electrode during a transition between electrode combinations. This arrangement of electrode combinations may also help a user (e.g., patient 12 or a clinician) better comprehend the manner in which the electrode combinations are being tested.

An arrangement in which at least some of the adjacent electrode combinations of the set include at least one shared anode electrode and at least one shared cathode electrode, the impact from incremental changes in anodic amplitude, cathodic amplitude, or both, may be minimized, e.g., when transitioning between electrode combinations. In addition, the arrangement in which at least some of the adjacent electrode combinations of the set include at least one shared anode electrode and at least one shared cathode electrode may help minimize the likelihood that overstimulation will occur suddenly from one step to another.

In some examples, at least some of the electrode combinations are tested at a plurality of different anodic and cathodic amplitude combinations. For a particular electrode combination, IMD 14 may assign each anode in the electrode combination an anodic amplitude and assign each cathode in the combination a cathodic amplitude, and control the sourcing and sinking of electrical stimulation via the anode and cathode electrodes in accordance with the assigned anodic and cathodic amplitudes in order to deliver electrical stimulation to patient 12 via the electrode combination. An anodic or cathodic amplitude may be, for example, defined as a portion of the total current or charge delivered by the electrode, displayed as a percentage contribution or effective amplitude of the electrode.

In some example techniques for testing a predefined set of electrode combinations on patient 12, IMD 14 incrementally adjusts (i.e., increase or decreases) the anodic and cathodic amplitudes, such that at least some of the electrode combinations are tested using a plurality of different anodic and cathodic amplitude combinations. While the active anode and cathode electrodes in the electrode combination remain the same, IMD 14 incrementally increases or decreases at least one anodic amplitude and/or at least one cathodic amplitude during the test period for the electrode combination. In addition to, or instead of, the logical and efficient arrangement of electrode combinations discussed above, the electrode combinations of a predefined set can be arranged such that at least some electrode combinations may be transitioned to the next electrode combination in the order by an incremental adjustment to at least one anodic amplitude and/or at least one cathodic amplitude. This technique is described in further detail with respect to FIGS. 10A-11D. This arrangement of electrode combinations within a predefined set may enable IMD 14 to transition between electrode combinations with minimal or no discomfort to patient 12.

In addition, in some examples, the electrode combinations of the set are arranged in the predetermined order such that electrode combinations being tested are propagated down the lead, e.g., from a proximal end of the lead to a distal end of the lead or vice versa, as electrode combinations are tested in the predetermined order. In this way, a set of test electrode combinations may be configured to test electrode combinations at different target tissue sites in a logical and efficient manner. The proximal end of lead 16A may be the end closest to IMD 14 when IMD 14 is electrically connected to IMD 14.

In some examples, the set of electrode combinations in the predetermined order define a predetermined sequence of electrode patterns, each electrode pattern defining a relative arrangement between one or more anodes and one or more cathodes of the respective electrode pattern. The electrode patterns in the sequence are predetermined, and, therefore, define a predetermined group of electrode patterns. An electrode combination may be defined by a subset of electrodes of lead 16A, and the polarities of the particular electrodes. Thus, the electrode combination may be defined by a subset of electrodes of lead 16A and an electrode pattern. The length of the sequence (e.g., the number of electrode combinations in the sequence) can be any suitable size, such as eight electrode combinations, 10 electrode combinations, 16 electrode combinations, 20 electrode combinations, or 32 electrode combinations, although the sequence can include a fewer or greater number of electrode combinations. The sequence may be selected in some examples such that adjacent electrode combinations have different electrode patterns.

Electrode patterns of the predetermined group can be selected using any suitable technique. The electrode patterns may be, for example, a group of electrode patterns known to the clinician or to another entity (e.g., a manufacturer of IMD 14 or leads 16) to be potentially effective or effective for a particular patient condition or one or more symptoms, based on historical data, computer modeling of the electrical stimulation, user experience data, or any combination thereof. In some examples, the electrode patterns of the predetermined group are preselected, e.g., by a manufacturer of IMD 14, and may not be modified by the user. In other examples, the user may select the electrode patterns, e.g., by selecting between a bipolar sequence and a unipolar sequence (e.g., cathodes on a lead and anodes on IMD 14 housing).

In some examples, every electrode pattern of the group of electrode patterns that define the predefined set of electrode combinations are selected such that the anode and cathode electrodes of every electrode pattern in the predefined set are programmed together on adjacent electrodes without any inactive (also referred to as "off" or "unused") electrodes between the active electrodes. As a result, in some examples, every electrode combination in the predefined set includes active electrodes that are immediately adjacent to each other and interrupted by inactive electrodes. This type of arrangement of anode and cathode electrodes may minimize the area of activation of the neurons as the electrode combinations propagate down the electrode array. As a result, the electrical stimulation via may be more precise.

In other examples, however, the group of electrode patterns includes at least one electrode pattern in which at least two active electrodes are separated by at least one inactive electrode, as shown in FIGS. 6-11D with electrode combinations C and CC, which each have one inactive electrode between active electrodes.

In some examples, at least one electrode pattern the predetermined group may appear multiple times at different positions in the predetermined sequence. For example, the predetermined sequence may be comprised of a repeating sub-sequence of electrode patterns (e.g., a sequence cycled through at least twice when all of the electrode combinations of the set are tested). The sub-sequence of electrode patterns may be repeated as, for example, test electrode combinations are propagated down lead 16A. Thus, in some examples in which programmer 18 tests a predefined set of electrode combinations on patient 12, programmer 18 automatically selects (e.g., with little to no user intervention) a plurality of different electrode combinations of the set by at least moving one or more electrode patterns (e.g., two or more patterns) down lead 16A in a systematic manner, e.g., from a proximal end of lead 16A to a distal end of lead 16A, or vice versa. In these examples, the position of a particular electrode pattern in the sequence may indicate the axial position along lead 16A at which the electrode pattern is tested on patient 12. In other examples, however, the plurality of electrode patterns may be arranged in the sequence in a non-repeating order.

Lead 16A (as well as lead 16B) defines a plurality of levels of electrodes, each level including at least one electrode and being separated from an adjacent level in an axial direction (e.g., in a direction substantially parallel to a longitudinal axis of lead 16A, the longitudinal axis extending between a proximal end and a distal end of lead 16A). As two or more electrode patterns are moved down lead 16A, the electrode patterns are moved through the levels of lead 16A, e.g., from a proximal end of the lead to a distal end of the lead or vice versa. Moving two or more electrode patterns down lead 16A in a systematic manner results in a plurality of different electrode combinations. Levels of leads 16A, 16B may correspond to each other based on the relative alignment of the levels when leads 16A, 16B are implanted in patient 12. For example, if each of leads 16A includes four levels of electrodes, leads 16A, 16B may be implanted such that a first level of electrodes of lead 16A substantially aligns with (e.g., adjacent to) and corresponds to a first level of electrodes of lead 16B, such that a second level of electrodes of lead 16A substantially aligns with (e.g., is adjacent to) and corresponds to a second level of electrodes of lead 16B, and so forth. When leads 16A, 16B are implanted in patient 12, electrodes on adjacent leads 16A, 16B may not be precisely aligned, e.g., at the same height, but may still be considered to be at corresponding levels.

Ordering electrode combinations of the set such that two or more electrode patterns are shifted down lead 16A in a systematic manner enables the electrode patterns to be tested at different axial positions (e.g., positions along a longitudinal axis) of lead 16A in an orderly and logistic manner without moving lead 16, thereby providing an efficient way to explore the electrode space defined by a given lead 16 (or set of leads 16), allowing many electrode patterns to be tried at different axial positions in quick succession. When lead 16A is implanted in patient 12, electrodes at different axial positions of lead 16A may be proximate to different tissue sites. Because the tissue site may affect the efficacy of electrical stimulation, the efficacy of electrical stimulation may differ depending on the axial position of the electrodes with which IMD 14 delivers electrical stimulation. In this way, the axial position along lead 16A may affect the therapeutic efficacy of a particular electrode pattern.

The electrode combinations in the set, as well as the order of electrode combinations within the set, provide a useful starting point for identifying one or more electrode combinations for delivering efficacious electrical stimulation therapy to patient 12. The automatic selection of electrode combinations for testing by IMD 14 or programmer 18 may be more efficient (e.g., consume less time) than the manual selection of the same electrode combinations by a clinician. Programmer 18 may be configured such that once the testing is initiated, e.g., by a clinician interacting with programmer 18, programmer 18 automatically controls IMD 14 to generate and deliver electrical stimulation therapy to patient 12 via each electrode combination of a plurality of predetermined electrode combinations in the predetermined order. The automated selection of electrode combinations to test may eliminate or at least reduce the interaction required by the clinician during a programming session.

The testing of a set of electrode combinations defining a sequence of two or more electrode patterns may also be more efficient than a technique in which a plurality of electrode patterns are tested by testing one electrode pattern at a time by shifting the electrode pattern down the lead to test the electrode pattern at different axial positions. Rather than moving one electrode pattern at a time to different axial positions and consuming time to shift the same electrode pattern to the different axial positions and repeating the process for another electrode pattern, some example techniques described herein interleave the electrode patterns being tested as electrode combinations propagate down the lead. The electrode combinations in the predefined set being tested may be ordered such that electrode combinations include at least one anode or cathode from the previous electrode combination in the predetermined order, such that the transitions between electrode combinations is relatively fluid and efficient. This type of transition between electrode combinations may not be possible if one electrode pattern at a time is tested on patient 12.

In some examples, IMD 14 may generate the electrical stimulation signal delivered via each of the electrode combinations of a set with a common set of other stimulation parameter values (e.g., current or voltage amplitude and frequency). In this way, the variable that is changing may be limited to the electrodes with which electrical stimulation is delivered to patient 12. In addition, another variable that may change during the testing of a predefined set of electrode combinations is the distribution of amplitude between the anodes and between the cathodes for a particular electrode combination. As discussed above, in some examples, at least some of the electrode combinations use a plurality of different anodic and cathodic amplitude settings. The efficacy of electrical stimulation according to a particular electrode combination may vary depending on the anodic amplitudes and cathodic amplitudes of each of the active electrodes. Thus, testing at least some electrode combinations using a plurality of different anodic and cathodic amplitude setting may help more thoroughly evaluate the efficacy of a particular electrode combination and identify an efficacious anodic amplitudes and cathodic amplitudes.

In other examples, IMD 14 may generate the electrical stimulation signal delivered via at least two of the electrode combinations of a set with different stimulation parameter values. Different stimulation parameter values may be selected if, for example, one set of other stimulation parameter values would result in uncomfortable stimulation for one or more of the electrode combinations due to the relative position between the electrodes of the electrode combination and the tissue of patient 12.

In some examples, during the automatic scanning through the electrode combinations of a predefined set, a user (e.g., a clinician or patient 12) may interact with programmer 18 to modify the stimulation parameter values with which IMD 14 generates the electrical stimulation signal, e.g., based on the perception of stimulation by patient 12. For example, the user can increase or decrease the intensity of stimulation (e.g., by increasing or decreasing the total stimulation amplitude) to maintain comfortable sensations that are strong enough to evaluate the efficacy of the electrode combinations. In some examples, the intensity is only increased for the present electrode combination being tested by IMD 14 when the user input modifying the amplitude was received, and then returned to a baseline level for subsequently tested electrode combinations (unless user input is received to change the intensity of stimulation for those other electrode combinations). In other examples, programmer 18 (or IMD 14) also applies the modified stimulation amplitude to the remaining electrode combinations in the set to be tested on patient 12.

Programmer 18 can control when the user modifies the stimulation parameter values during the automatic scanning through the electrode combinations of a set. For example, programmer 18 may be configured such that the user may only modify the stimulation parameter values when IMD 14 is not actively changing electrode combinations or anodic and cathodic amplitude settings, e.g., when the automatic scanning is paused.

In some examples, the efficiency of the electrode combination testing process may be further improved by reducing the amount of input from patient 12. For example, patient 12 may only provide efficacy feedback when efficacious electrical stimulation is perceived, e.g., by providing input to programmer 18 (directly or indirectly, e.g., via a clinician). In response to receiving the input, programmer 18 may store information identifying the electrode combination that the input is associated with, e.g., by marking the electrode combination with which IMD 14 was delivering electrical stimulation when the efficacious electrical stimulation was perceived by patient 12. In examples in which at least some electrode combinations are tested at a plurality of different anodic amplitude and cathodic amplitude combinations, the information identifying the electrode combination can include information identifying the anodic amplitude and cathodic amplitude combination associated with the input.

After the testing of the set of electrode combinations, the marked electrode combinations (and any associated information, such as the anodic amplitude and cathodic amplitude combination) may then be used to program one or more therapy parameters, for identification of additional electrode combinations to test on patient 12, or any other use. In this way, patient 12 may only intervene with efficacy feedback when efficacious electrical stimulation is perceived and system 10 may otherwise automatically test the set of electrode combinations. The efficacy of the electrical stimulation may be, for example, based on the reduction in one or more symptoms of a patient condition, relatively low side effects from the electrical stimulation therapy, or some combination of both. When patient 12 intervenes with the efficacy feedback, the clinician may pause the delivery of test electrical stimulation according to the set of electrode combinations, or may let the automatic testing of the set of electrode combinations continue without pausing or otherwise stopping the automatic testing process.

In contrast to a system in which a clinician manually selects an electrode combination, and then patient 12 provides efficacy feedback for the selected combination prior to the selection of another electrode combination by the clinician, prior to the delivery of electrical stimulation by IMD 14 via another electrode combination, or both, system 10 is configured to automatically test a set of electrode combinations in a predetermined order without requiring the clinician to modify the electrode combinations, without requiring the clinician to manually control IMD 14 to deliver electrical stimulation via each electrode combination, or without requiring patient 12 to provide input for each electrode combination prior to testing another electrode combination may be more efficient. The efficiency may be at least partially attributable to the reduction in the amount of time between the testing of different electrode combinations. In addition, the time required to receive patient input for electrode combinations that are not efficacious may be eliminated. In some techniques described herein, programmer 18 or a clinician may determine that an electrode combination being tested is not efficacious unless the patient indicates otherwise. This may help reduce the total amount of time consumed to test a plurality of electrode combinations.

Some clinicians or patients may prefer to provide efficacy input for each tested electrode combination. Thus, in other examples described herein, patient 12 may provide feedback for each tested electrode combination. Even with feedback from patient 12 for each tested electrode combination, rather than for only the efficacious electrode combinations, the automatic testing of a set of electrode combinations in a predetermined order and without requiring clinician intervention to select a next electrode combination to test may be more efficient than existing devices, systems, and techniques in which each electrode combination is manually selected and a clinician is required to take some action between tested electrode combinations to control the delivery of electrical stimulation via an electrode combination to be tested.

Figure 2:
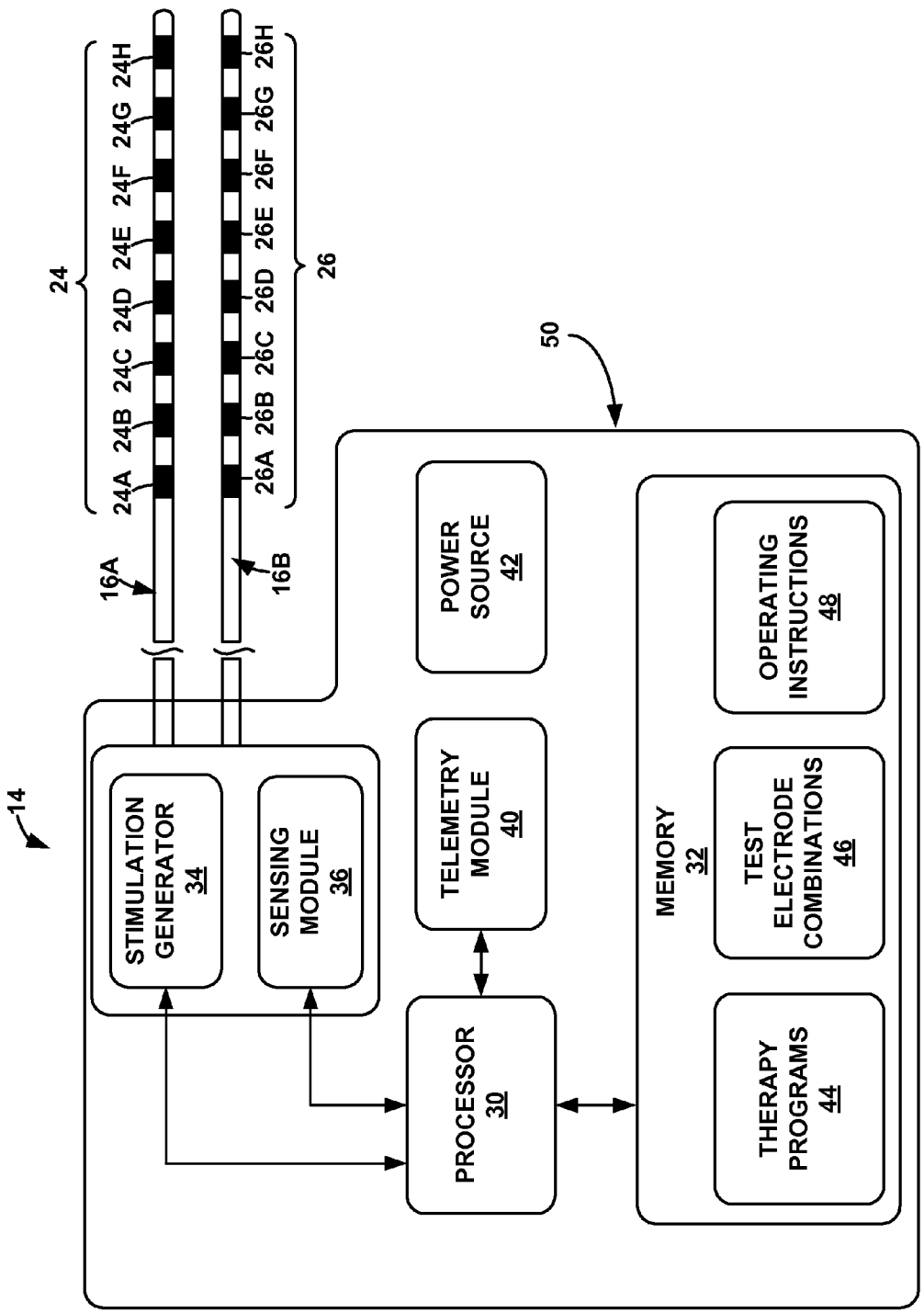
FIG. 2 is functional block diagram illustrating components of an example medical device.

FIG. 2 is functional block diagram illustrating components of an example IMD 14. FIG. 2 also illustrates leads 16A, 16B and the respective sets of electrodes 24A-24H (collectively referred to as "electrodes 24"), 26A-26H (collectively referred to as "electrodes 26"). In the example shown in FIG. 2, IMD 14 includes processor 30, memory 32, stimulation generator 34, sensing module 36, telemetry module 40, and power source 42. Memory 32, as well as other memories described herein, may include any one or more volatile or non-volatile media, such as a random access memory (RAM), read only memory (ROM), non-volatile RAM (NVRAM), electrically erasable programmable ROM (EEPROM), flash memory, and the like. Memory 32 may store computer-readable instructions that, when executed by processor 30, cause IMD 14 to perform various functions described herein.

In the example shown in FIG. 2, the set of electrodes 24 of lead 16A includes electrodes 24A, 24B, 24C, 24D, 24E, 24F, and 24H, and the set of electrodes 26 of lead 16B includes electrodes 26A, 26B, 26C, 26D, 26E, 26F, and 26H. As shown in FIGS. 1 and 2, leads 16 can be implanted in patient 12 such that they are substantially parallel to each other and spinal cord 18, on substantially opposite sides of spinal cord 18, at approximately the same height relative to spinal cord 18, and oriented such that the distal ends of leads 16 are higher relative to the spinal cord than the proximal ends of leads 16. Therefore, the illustrated configuration of electrodes 24, 26 may be described as a two-by-eight, side-by-side, upwardly oriented configuration. Such a configuration may be useful for some types of SCS therapy. Other configurations are also contemplated and may depend on the patient condition for which system 10 is implemented to treat. In addition, in some examples, system 10 includes only one lead 16 (which may define a one-dimensional or two-dimensional array of electrodes) or more than two leads 16, such as three leads.

In the example shown in FIG. 2, memory 32 stores therapy programs 44, electrode combinations 46, and operating instructions 48, e.g., in separate memories within memory 32 or separate areas within memory 32. Each stored therapy program 44 defines a particular program of therapy in terms of respective values for a set of electrical stimulation parameters, such as an electrode combination, current or voltage amplitude, and, if stimulation generator 34 generates and delivers stimulation pulses, the therapy programs may define values for a pulse width and pulse rate of a stimulation signal. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Electrode combinations 46 stored by memory 32 include a plurality of predetermined electrode combinations to be tested (also referred to herein as "test electrode combinations") on patient 12 to identify an efficacious electrode combination, e.g., during a programming session with a clinician. Electrode combinations 46 may be organized as one or more sets of predetermined electrode combinations, where the electrode combinations of a particular set are arranged in a predetermined order, as discussed above. The predetermined electrode combinations of a particular set may include electrode combinations selected and arranged in the set, for example, at some point prior to initiating the automatic testing of the electrode combinations in the set on patient 12. In examples in which IMD 14 stores test electrode combinations 46, processor 30 may initiate the delivery of electrical stimulation via a particular set of electrode combinations in response to receive a control signal from programmer 18 or another device.

The electrode combinations that are organized into a common set of electrode combinations may be selected (by a clinician, by a distributor of IMD 14, or another entity) based on one or more criteria, such as, but not limited to, the electrode patterns defining the electrode combinations. As discussed above, the electrode patterns may be two or more electrode patterns known to the clinician or to another entity to be potentially effective or effective for a particular patient condition or one or more symptoms, based on historical data.

In other examples, IMD 14 does not store test electrode combinations 46, but, rather, the test electrode combinations may be stored by another device, such as programmer 18 (FIG. 1). In these examples, programmer 18 (or the other device) may transmit (e.g., via a wireless communication link) the test electrode combinations to IMD 14. Processor 30 may receive the test electrode combinations from programmer 18 via telemetry module 40 and control stimulation generator 34 to generate and deliver electrical stimulation therapy to patient 12 via each of the electrode combinations, e.g., in accordance with one or more example techniques described herein.

Operating instructions 48 guide general operation of IMD 14 under control of processor 30, and may include instructions for controlling the delivery of electrical stimulation to patient 12 via each of the plurality of test electrode combinations 46. The instructions for controlling the delivery of electrical stimulation to patient 12 via each of the plurality of test electrode combinations 46 may include, for example, the duration of time electrical stimulation is delivered to patient 12 via each test electrode combination (also referred to herein as a "test period"), and, in some examples, the predetermined order in which the test electrode combinations of a set are tested. In addition, the instructions for controlling the delivery of electrical stimulation to patient 12 can include the instructions with which IMD 14 incrementally modifies at least one anodic amplitude or at least one cathodic amplitude for a particular electrode combination during the test period for the electrode combination. Such information may include the minimum amplitude increments and the time between amplitude adjustments.

In other examples, however, the incremental adjustments to the at least one anodic amplitude or at least one cathodic amplitude is controlled by programmer 18 or another device, such as a remote computing device.

Stimulation generator 34 is electrically coupled to each of the electrodes 24, 26 via conductors of the respective lead 16A, 16B. Stimulation generator 34 may include stimulation generation circuitry configured to generate stimulation pulses or waveforms and circuitry for switching stimulation across different electrode combinations, e.g., in response to control by processor 30. Stimulation generator 34 is configured to, under the control of processor 30, generate electrical stimulation signals and deliver the electrical stimulation signals to patient 12 via selected electrode combinations. In some examples, stimulation generator 34 generates and delivers electrical stimulation signals to one or more target tissue sites in patient 12 via a select electrode combination based on one or more stored therapy programs 44. The target tissue sites for stimulation signals or other types of therapy and stimulation parameter values may depend on the patient condition for which therapy system 10 is implemented to manage.

Stimulation generator 34 may be a single channel or multi-channel stimulation generator. In particular, stimulation generator 34 may be capable of delivering, a single stimulation pulse, multiple stimulation pulses or a continuous signal at a given time via a single electrode combination or multiple stimulation pulses at a given time via multiple electrode combinations. In examples in which stimulation generator 34 is a single channel stimulation generator, stimulation generator 34 is configured to output electrical stimulation signals via a single channel. In examples in which stimulation generator 34 is a multi-channel stimulation generator, stimulation generator 34 is configured to output electrical stimulation signals via a single channel (e.g., via a single electrode combination) or via multiple channels (e.g., via multiple electrode combinations) at different times (e.g., on a time-interleaved basis) or simultaneously using a single stimulation engine or multiple stimulation engines.

In some examples, stimulation generator 34 includes a plurality of stimulation engines that provide a current source and a current sink for each electrode 24, 26 electrically coupled to IMD 14 to be driven by the stimulation engines. In examples in which stimulation generator 34 is configured to deliver current-controlled electrical stimulation, processor 30 is configured to control the stimulation engines to selectively source or sink current via each electrode at a variety of current amplitudes. In other examples, stimulation generator 34 is configured to deliver voltage-controlled electrical stimulation.

In other examples, stimulation generator 34 includes a fewer number of stimulation engines, e.g., one or more stimulation engines are shared for two or more electrodes, and IMD 14 includes a switch module, and processor 30 may be configured to control the switch module to apply the stimulation signals generated by stimulation generator 34 to selected combinations of electrodes 24, 26. The switch module may be, for example, a switch array, switch matrix, multiplexer, or any other type of switching module configured to selectively couple stimulation energy to selected electrodes 24, 26. In some examples in which IMD 14 includes a switch module, stimulation generator 34 and the switch module may be configured to deliver multiple channels on a time-interleaved basis. For example, the switch module may serve to time divide the output of stimulation generator 34 across different electrode combinations at different times to deliver multiple programs or channels of stimulation energy to patient 12.

During a programming session for selecting one or more efficacious electrode combinations for later storage as part of one or more therapy programs 44, stimulation generator 34 may, under the control of processor 30 or programmer 18, or both, automatically generate and deliver electrical stimulation therapy to patient 12 via each electrode combination of a predefined set of test electrode combinations 46 stored by memory 62 (or another memory). In examples in which the plurality of test electrode combinations are tested in a predetermined order, processor 30 may control the order based on the order in which the test electrode combinations are stored by memory 32, based on the order provided by programmer 18, based on the order stored by operating instructions 48, or based on other control information.

The processors described in this disclosure, including processor 30, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 30 is configured to control stimulation generator 34 according to therapy programs 44 stored in memory 32 to apply particular stimulation parameter values specified by one or more programs, such as amplitude, pulse width, and pulse rate.

In the example shown in FIG. 2, sensing module 36 is electrically coupled to each of the electrodes 24, 26 via conductors of the respective lead 16A, 16B. Although not shown in FIG. 2, IMD 14 may include a switch array or the like to selectively electrically connect electrodes 24, 26 to stimulation generator 34 or sensing module 36. Sensing module 36, under the control of processor 30, is configured to sense one or more physiological parameters of patient 12 via a selected subset of electrodes 24, 26 or with one or more electrodes 24, 26 and at least a portion of a conductive outer housing 50 of IMD 14, an electrode on an outer housing of IMD 14 or another reference. The sensed physiological parameters may be used for one or more purposes, such as to control therapy delivery by IMD 14, determine the efficacy of test electrode combinations, or monitor a health status of patient 12. In some examples, a set of electrode combinations may be automatically tested on patient 12 more than one time, e.g., for each of a plurality of different posture states (e.g., a patient posture or a combination of posture and activity) of patient 12, and sensing module 36 may be configured to generate a signal indicative of the patient posture state. For example, sensing module 36 may include one or more accelerometers, such as a three-axis accelerometer, capable of detecting static orientation or vectors in three-dimensions.

Although sensing module 36 is incorporated into a common housing 50 with stimulation generator 34 and processor 30 in FIG. 2, in other examples, sensing module 36 is in a separate outer housing from outer housing 34 of IMD 14 and communicates with processor 30 via wired or wireless communication techniques. In other examples, system 10 does not include sensing module 36.

Telemetry module 40 is configured to support wireless communication between IMD 14 and an external programmer 18 or another computing device under the control of processor 30. Processor 30 of IMD 14 may receive, e.g., as updates to stored therapy programs 44, values for various stimulation parameters such as amplitude and electrode combination, from programmer 18 via telemetry module 40. The updates to the therapy programs may be stored within therapy programs 44 portion of memory 32. In addition, in some examples, processor 30 receives a plurality of test electrode combinations, other stimulation parameter values for use during the testing of electrode combinations, or both, from programmer 18 via telemetry module 40. Telemetry module 40 in IMD 14, as well as telemetry modules in other devices and systems described herein, such as programmer 18, may accomplish communication by RF communication techniques. In addition, telemetry module 40 may communicate with external medical device programmer 18 via proximal inductive interaction of IMD 14 with programmer 18. Accordingly, telemetry module 40 may send information to external programmer 18 on a continuous basis, at periodic intervals, or upon request from IMD 14 or programmer 18. For example, processor 30 may transmit brain state information 76 to programmer 18 via telemetry module 40.

Power source 42 is configured to deliver operating power to various components of IMD 14. Power source 42 may include a small rechargeable or non-rechargeable battery and a power generation circuit to produce the operating power. Recharging may be accomplished through proximal inductive interaction between an external charger and an inductive charging coil within IMD 14.

Figure 3:
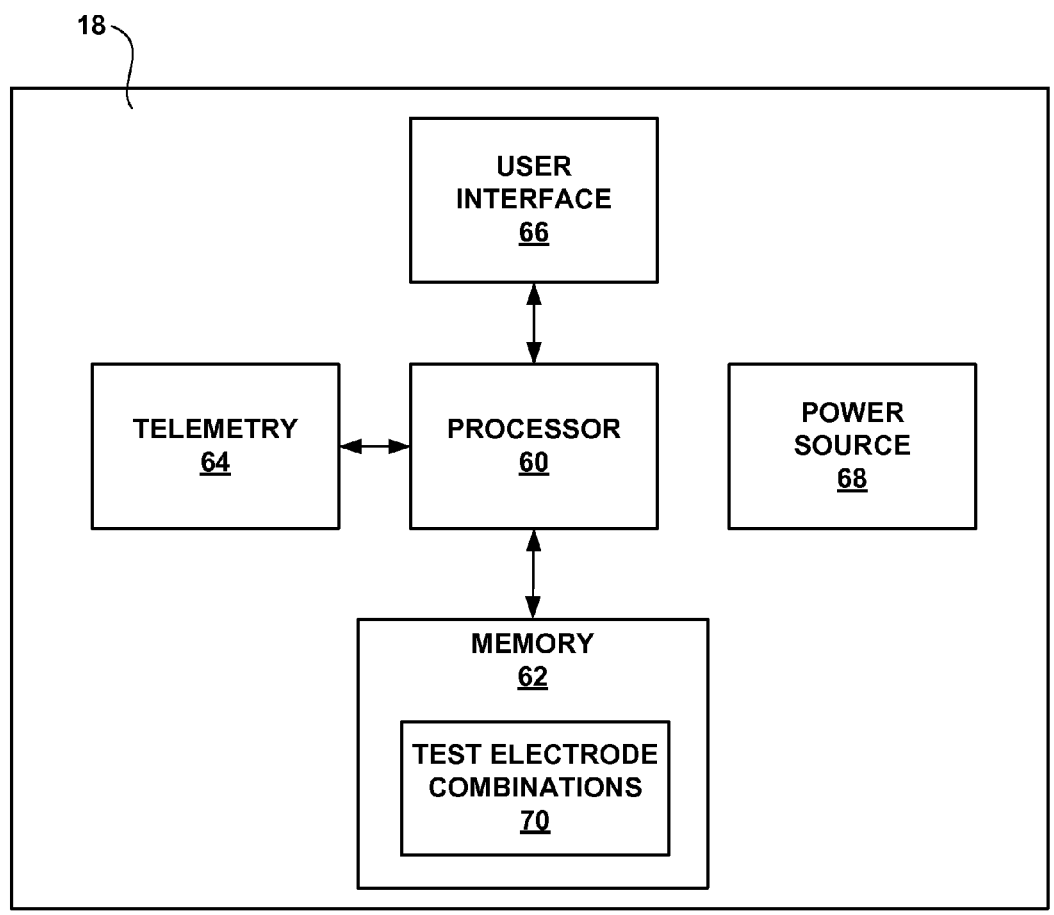
FIG. 3 is a functional block diagram illustrating components of an example medical device programmer.

FIG. 3 is a functional block diagram illustrating components of an example medical device programmer 18 (FIG. 1). Programmer 18 includes processor 60, memory 62, telemetry module 64, user interface 66, and power source 68. Processor 60 is configured to control telemetry module 64 and user interface 66, and store and retrieve information and instructions to and from memory 62. Programmer 18 may be configured for use as a clinician programmer or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60. In some examples, processor 60 of programmer 18 may perform any part of the techniques described above with respect to processor 30 of IMD 14. In addition, in some examples, processor 30 may perform any part of the techniques described with respect to processor 60 of programmer 18.

A user, such as a clinician or patient 12, may interact with programmer 18 via user interface 66. User interface 66 includes a display (not shown), such as a liquid crystal display (LCD) or light emitting diode (LED) display or other type of screen, with which processor 60 may present information related to therapy, information that indicates electrode combinations of a set of electrode combinations available for testing on patient 12, electrode combinations tested on patient 12, or efficacy information for tested electrode combinations (e.g., patient efficacy ratings, physiological data, or any combination thereof). In addition, user interface 66 may include an input mechanism configured to receive input from the user. The input mechanisms may include, for example, buttons, a keypad (e.g., an alphanumeric keypad), a peripheral pointing device, a touchscreen display, or another input mechanism that allows the user to navigate though user interfaces presented by processor 60 of programmer 18 and provide input.

In some examples, the user may interact with user interface 66 to control the therapy delivery by IMD 14. For example, the user may provide input via user interface 66 to adjust the overall intensity of the electrical stimulation during the testing of a plurality of electrode combinations of a predefined set. The user may, for example, decrease the stimulation amplitude when the electrical stimulation become uncomfortable or increase the overall intensity of the stimulation when patient 12 can no longer perceive the electrical stimulation or desires a higher intensity electrical stimulation. In response to such user input, processor 60 may control IMD 14 (e.g., by transmitting a control signal to IMD 14) to adjust the amplitude of electrical stimulation delivered via the electrode combinations of the set of electrode combinations. As discussed above, programmer 18 may temporarily suspend testing of a plurality of electrode combinations to hold the electrode combination being tested steady while a user modifies one or more stimulation parameter values.

If programmer 18 includes buttons and a keypad, the buttons may be dedicated to performing a certain function, i.e., a power button, or the buttons and the keypad may be soft keys that change function depending upon the section of the user interface currently viewed by the user. In addition, or instead, the screen (not shown) of programmer 18 may be a touch screen that allows the user to provide input directly to a GUI presented on the display. The user may use a stylus or their finger to provide input to the display. In other examples, user interface 66 also includes audio circuitry for providing audible notifications, instructions or other sounds to patient 12, receiving voice commands from patient 12, which may be useful if patient 12 has limited motor functions.

The user may also interact with user interface 66 to manually change the stimulation parameter values of a therapy program, manually select therapy programs, generate new therapy programs, transmit new therapy programs to IMD 14, view therapy information, control the automatic testing of a set of electrode combinations by programmer 18 and IMD 14 (e.g., initiate the testing process, pause the testing process, or permanently stop the testing process), or otherwise communicate with IMD 14. An example GUI that may be displayed via a display of user interface 66 for controlling the automatic testing of a set of electrode combinations is described below with respect to FIG. 12.

In some examples, at least some of the control of therapy delivery by IMD 14 may be implemented by processor 60 of programmer 18. For example, processor 60 may control the therapy parameter values, timing, or both, of the generation and delivery of electrical stimulation to patient 12 during a programming session in which a plurality of electrode combinations are tested on patient 12. As another example, processor 60 may control incremental changes to the distribution of amplitude between anodes and between cathodes of a particular electrode combination, i.e., changes to the anodic amplitude settings or cathodic amplitude settings, during the testing of the electrode combination. As discussed above, the automatic modification to one or more anodic amplitudes, one or more cathodic amplitudes, or both, during the testing of a particular electrode combination may enable the electrode combination to be more thoroughly tested in an efficient manner. In other examples, processor 30 of IMD 14 may control one or more these aspects of the generation and delivery of electrical stimulation to patient 12 during the programming session.

Memory 62 is configured to store data. Memory 62 may include any volatile or nonvolatile memory, such as RAM, ROM, EEPROM or flash memory. Memory 62 may also include a removable memory portion that may be used to provide memory updates, increases in memory capacities, or storage of sensitive patient data. Memory 62 may store instructions for execution by processor 60, such as, but not limited to, instructions for operating user interface 66 and telemetry module 64, and for managing power source 68. Memory 62 may also store therapy data retrieved from IMD 14 during the course of therapy or during a programming session.

Figure 4A:
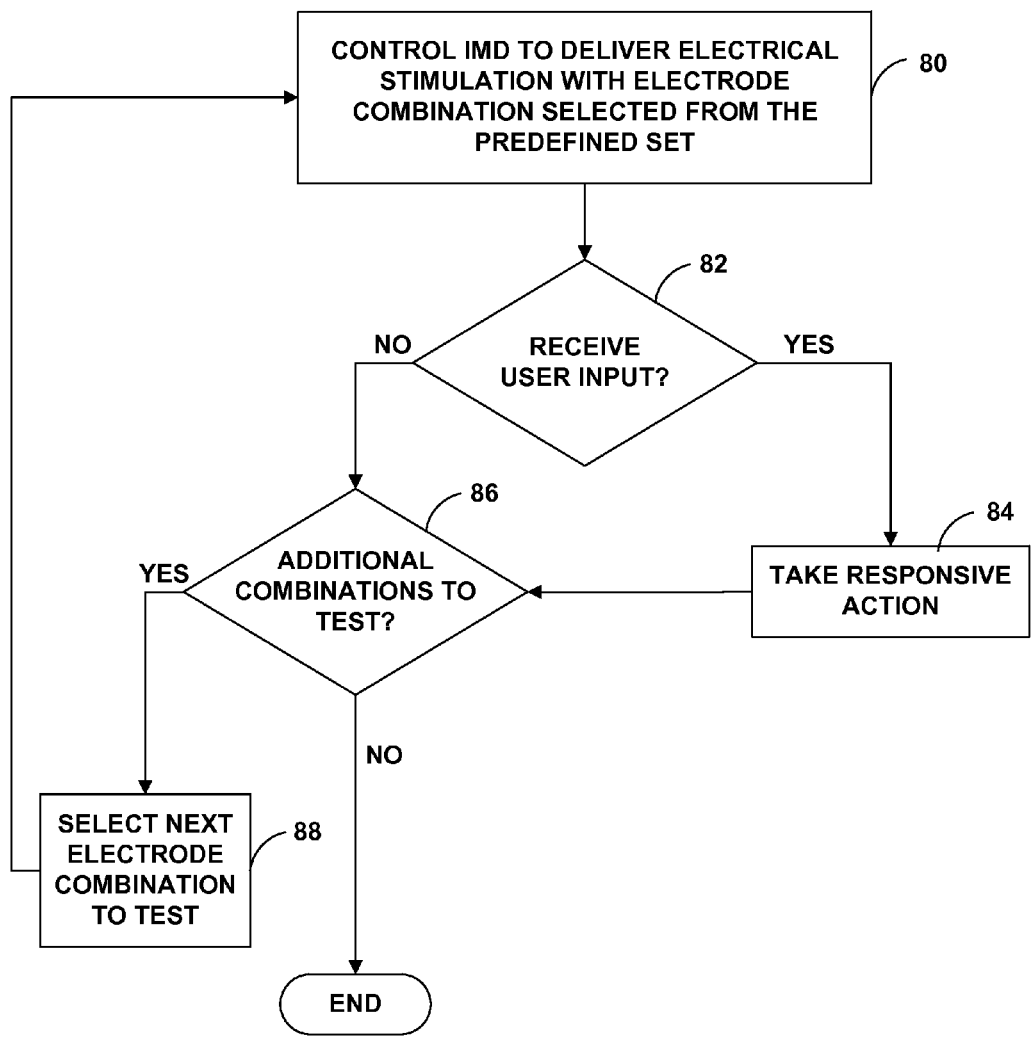
FIGS. 4A and 4B are flowcharts illustrating example techniques for identifying one or more electrode combinations that may provide efficacious therapy for a patient.

Memory 62 may store instructions for execution by processor 60 to implement the electrode combination search techniques described herein, including the search technique described with respect to FIG. 4A. In the example shown in FIG. 3, memory 62 stores test electrode combinations 70, which includes one or more predefined sets of electrode combinations to be tested on patient 12 in order to identify one or more efficacious electrode combinations, e.g., during a programming session with a clinician. Electrode combinations 70 can be the same as electrode combinations 46 described with respect to FIG. 2. As discussed above, in some examples, test electrode combinations 70 are stored by only programmer 18 (in which case IMD 14 does not store test electrode combinations 46), only IMD 14 (in which case programmer 18 does not store test electrode combinations 70), or both IMD 14 and programmer 18.

Memory 62 may also store information relating to the plurality of tested electrode combinations, which may facilitate the identification of efficacious electrode combinations by the clinician. The clinician may reference the stored information for one or more purposes, such as to determine one or more electrode combinations for programming IMD 14 for chronic stimulation therapy or for further trialing on patient 12. The information can include efficacy information, such as, but not limited to, any one or more of efficacy markers, subjective efficacy ratings provided by patient 12 for a specific tested electrode combination or one or more sensed physiological parameter values indicative of the efficacy of the associated electrode combination. An efficacy rating provided by patient 12 may take any suitable format. In some examples, the efficacy rating can be any one or more of a numerical rating on a predefined scale (e.g., a scale of 1-10), a another type of rating (e.g., a rating using the Wong-Baker FACES Pain Rating Scale), or a pain map that indicates the area of paresthesia resulting from the delivery of electrical stimulation via a particular electrode combination. The rating can indicate the reduction in symptoms of the patient condition, the severity of the side effects resulting from the electrical stimulation therapy, or both.

Processor 60 may be configured to present, e.g., via a display of user interface 66, a list of tested electrode combinations and their associated information (e.g., efficacy information), where available. For example, in some examples, a user may interface with user interface 66 to input a request to view the predefined set of test electrode combinations, which can include, in some examples, an indication of the automatic anodic and/or cathodic amplitude adjustments for each of the test electrode combinations for which the amplitudes will be automatically adjusted. In response to receiving the user input, processor 60 may generate and present a display via user interface 66 that indicates the electrode combinations (which can be identified by name, diagram, or any other identifier) of the set. In addition, in some examples, processor 60 is configured to, in response to receiving a user request via user interface 66, order the list according to the efficacy ratings or another parameter.

Programmer 18, alone or with the aid of a user, may create therapy programs that include the identified efficacious electrode combinations. Processor 60 may be configured to transmit the therapy programs to IMD 14, e.g., via the respective telemetry modules 64, 40.

Wireless telemetry in programmer 18 may be accomplished by RF communication or proximal inductive interaction of external programmer 18 with IMD 14. This wireless communication is possible through the use of telemetry module 64. Accordingly, telemetry module 64 may be similar to the telemetry module 40 of IMD 14. In other examples, programmer 18 may be capable of infrared communication or direct communication through a wired connection. In this manner, other external devices may be capable of communicating with programmer 18 without needing to establish a secure wireless connection.

Power source 68 is configured to deliver operating power to the components of programmer 18. Power source 68 may include a battery and a power generation circuit to produce the operating power. In some examples, the battery may be rechargeable to allow extended operation. In addition, programmer 18 may be directly coupled to an alternating current outlet to operate.

In some cases, external programmer 18 may be characterized as a physician or clinician programmer if it is primarily intended for use by a physician or clinician. In other cases, external programmer 18 may be characterized as a patient programmer if it is primarily intended for use by patient 12. A patient programmer is generally accessible to patient 12 and, in many cases, may be a portable device that may accompany the patient throughout the patient's daily routine. A physician or clinician programmer may support selection and generation of programs by a clinician for use by IMD 14, whereas a patient programmer may support adjustment and selection of such programs by patient 12 during ordinary use.

In some example techniques described herein for identifying one or more electrode combinations that may provide efficacious (e.g., beneficial) therapy for patient 12, IMD 14 delivers electrical stimulation to patient 12 via a plurality of electrode combinations of a predefined set in a predetermined order. For example, under the control of programmer 18, IMD 14 may deliver electrical stimulation energy via a first electrode combination of the set for a first test period, terminate delivery of stimulation via the first electrode combination, deliver electrical stimulation energy via a second electrode combination of the set for a second test period, terminate delivery of stimulation via the second electrode combination, deliver electrical stimulation energy via a third electrode combination of the set, and so forth, through an nth electrode combination of the set including n-number of electrode combinations, or until the clinician or patient 12 stops the testing. The clinician or patient may return to electrode combinations of the set that were marked as relatively efficacious and use those electrode combinations to identify one or more efficacious electrode combinations for patient 12.

The transitions between electrode combinations of a set in the predetermined order are selected to be efficient and comfortable to patient 12. For example, the n-number of electrode combinations may be arranged in the set such that adjacent electrode combinations share at least one anode electrode or at least one cathode electrode. In addition, the plurality of electrode combinations of the set include electrode combinations defined by a respective one of at least two electrode patterns, such that multiple electrode patterns may be tested on patient 12. In some examples, at least some of the electrode combinations of the set are tested at a plurality of different anodic and cathodic amplitude combinations. In these examples, the transitions between electrode combinations may also be relatively efficient and comfortable to patient 12 due to the manner in which at least one of the anodic amplitudes and/or at least one of the cathodic amplitudes are incrementally adjusted. For example, a transition from a first electrode combination to a second electrode combination may occur after an incremental adjustment to one or more of the anodic amplitudes or cathodic amplitudes of the first electrode combination. Thus, the transition to the second electrode combination may be relatively fluid.

FIG. 4A is a flowchart illustrating an example technique for identifying one or more electrode combinations that may provide efficacious therapy for patient 12. While different aspects of the technique shown in FIG. 4A are described with specific reference to processor 30 of IMD 14 and processor 60 of programmer 18, in other examples, any part of or the entire technique described with respect to FIG. 4A may be performed by processor 30 or processor 60 or a processor of another device. For example, part or all of the control of the testing of a set of electrode combinations may be performed by a computing device remotely located relative to programmer 18, IMD 14, or both, such as, but not limited to, a cloud computing device.

In some examples, the remote computing device may store one or more sets of test electrode combinations and communicate the one or more sets of test electrode combinations to programmer 18 or directly to IMD 14. In addition, or instead, the remote computing device may control incremental modifications to the anodic amplitudes and/or cathodic amplitudes during the delivery of electrical stimulation according to each tested electrode combination, e.g., as described with respect to FIGS. 10A-11D. The cloud computing device may be configured to be accessed by multiple individual devices (e.g., multiple programmers 18) as needed, where the individual devices may or may not be located within the same location. In this way, in some examples, the cloud computing device may service more than one clinic.

In the technique shown in FIG. 4A, processor 60 of programmer 18 controls IMD 14 to deliver electrical stimulation to patient 12 with an electrode combination selected from a predefined set of a plurality electrode combinations (80). Processor 60 may control IMD 14 using any suitable technique, such as by transmitting a control signal to processor 30 of IMD 14 via the respective telemetry modules 64, 40, and, in response to receiving the control signal, processor 30 may control stimulation generator 44 to generate and deliver electrical stimulation therapy to patient 12 via the selected electrode combination.

In some examples, processor 60 is configured to automatically control the timing, electrode combination, and anodic and cathodic amplitude settings with which IMD 14 delivers electrical stimulation to patient 12, i.e., without any user interaction other than user interaction starting the automatic scan through the predefined set of electrode combinations and user interaction stopping or pausing the automatic scan. This may help reduce the amount of time consumed to test the efficacy of the electrode combinations of the predefined set and limit the user interaction, which may help reduce the burden on a user. As discussed below, however, processor 60 may be configured to responsively control the automatic scan through the electrode combinations in response to intervening user input (received after the start of the automatic scan). However, processor 60 is configured, in some examples, to complete the automatic scan through the electrode combinations of the predefined set after processor 60 initiates the automatic scan, e.g., in response to user input, without any further user input after the scan is initiated. In this way, user interaction may not be required to proceed to the next step of the scan (e.g., the next test electrode combination).

In examples in which electrode combinations are propagated down lead 16A as the testing of the set progresses, the first electrode combination in the set of electrode combinations being tested on patient 12 may include the proximal-most electrode if the electrode combinations are shifted towards a distal end of lead 16A or the distal-most electrode if the electrode combinations are shifted towards a proximal end of lead 16A. However, the first electrode combination in the set may have other suitable configurations. For example, if the clinician only wants to test certain electrodes of lead 16A, the clinician may choose a starting electrode for the testing, and processor 60 may then start the automatic testing using the electrode combination of the set having a proximal-most cathode at the starting electrode in examples in which electrode combinations are shifted towards a distal end of lead 16A or a distal-most cathode at the starting electrode in examples in which electrode combinations are shifted towards a proximal end of lead 16A. For example, the steps required in the set of electrode combination shown in FIG. 6 and described in further detail below to propagate down the lead from electrode combination A to electrode combination E is different than the steps shown from electrode combination E to electrode combination M due to electrode combination A beginning with the cathode at the distal-most electrode.

IMD 14 may generate electrical stimulation energy delivered to patient 12 via the selected electrode combination using a stored set of stimulation parameter values or using stimulation parameter values transmitted to IMD 14 by processor 60 of programmer 18. The initial stimulation amplitude may be set at, for example, a level that is known to be at a perception intensity level (e.g., the lowest intensity level at which patient 12 may perceive the electrical stimulation) for the first electrode combination of the set or an average perception intensity level for a plurality of electrode combinations. In other examples, the initial stimulation amplitude may be set at zero and incrementally ramped up.

In some examples, IMD 14 is configured to control the anodic amplitude and cathodic amplitude assigned to each anode and cathode, respectively, of a particular electrode combination. As discussed above, in some examples, at least some of the electrode combinations are tested at a plurality of different anodic and cathodic amplitude combinations. IMD 14, alone or under the control of processor 60 of programmer 18 or another device, may initiate stimulation delivery according to a particular electrode combination at a starting anodic and cathodic amplitudes and then incrementally adjust the amplitudes according to a predefined schedule of amplitude adjustments. For example, a test period during which an electrode combination is tested on patient 12 may be divided into a plurality of time slots, and IMD 14 may increase or decrease the amplitudes by a minimum amplitude adjustment increment in each time slot according to the predefined schedule.

The minimum amplitude adjustment increments applied by IMD 14 to transition to a next time slot in the schedule may be substantially the same (e.g., equal or nearly equal) in some examples, and may be different in other examples. For example, the schedule may define two or more amplitude adjustment increments. In some examples, the schedule includes two amplitude adjustment increments that alternate, e.g., in alternating time slots. For example, to transition from a first time slot to a second time slot, IMD 14 (e.g., under the control of processor 60 or processor 30) may adjust at least one cathodic amplitude setting or at least one anodic amplitude setting, or both, by a first amplitude adjustment increment (e.g., 4%). In this example, to transition from the second time slot to a third time slot (immediately following the second time slot), IMD 14 may adjust at least one cathodic amplitude setting or at least one anodic amplitude setting, or both, by a second amplitude adjustment increment (e.g., 6%). Then, to transition from the third time slot to a fourth time slot (immediately following the third time slot), IMD 14 may adjust at least one cathodic amplitude setting or at least one anodic amplitude setting, or both, by the first amplitude adjustment increment (e.g., 4%). The first and second amplitude adjustments may alternate in this manner until the end of the schedule is reached.

In some examples, the steps defined by the predefined schedule of amplitude adjustments are arranged such that adjacent steps include at least one shared anode electrode and at least one shared cathode electrode. This sharing of anodes and cathodes may help reduce the impact to the electrical stimulation perceived by patient 12 resulting from the incremental changes in anodic amplitude, cathodic amplitude, or both, e.g., when transitioning between electrode combinations. In addition, the arrangement in which at least some of the adjacent electrode combinations of the set include at least one shared anode electrode and at least one shared cathode electrode may help minimize the likelihood that overstimulation will occur suddenly from one step of the schedule to another.

In some examples, the set of electrode combinations and, if present, the predefined schedule of amplitude adjustments, are stored by memory 62 of programmer 18, memory 32 of IMD 14, or both memories 32, 62. The other stimulation parameter values with which stimulation generator 34 generates the electrical stimulation energy delivered via the electrode combinations, such as the signal amplitude (current or voltage) and frequency, may be stored by memory 62 of programmer 18, memory 32 of IMD 14, or both memories 32, 62. Thus, in some examples, processor 60 transmits one or both of the electrode combination and other stimulation parameter values for generating the electrical stimulation energy to IMD 14, while, in other examples, the processor 60 controls delivery of electrical stimulation by IMD 14 by indicating which of the electrode combinations and other stimulation parameter values stored by memory 32 of IMD 14 should be selected by processor 30 of IMD 14.

As discussed above, an electrode combination can be characterized by the subset of electrodes 24 used to deliver electrical stimulation and the electrode pattern defined by the electrodes and the respective polarity of the electrodes. The set of electrode combinations for testing on patient 12 may be defined as a predetermined group of electrode patterns, the group including two or more electrode patterns, such as two, three, four, five, or more electrode patterns. These electrode patterns of the predetermined group may be referred to as "major" electrode patterns in that they define the plurality of electrode combinations that are identified for testing on patient 12. Any electrode patterns that may result from transitioning from a first electrode combination to a second electrode combination, e.g., resulting from the incrementally decreasing anodic and/or cathodic amplitudes of one or more active electrodes of the first electrode combination and the incremental increasing of anodic and/or cathodic amplitudes of one or more active electrodes of the second electrode combination, may be referred to as "minor" electrode patterns.

The two or more major electrode patterns in a predetermined group of test electrode patterns may be, for example, clinically relevant electrode patterns, and, therefore, a useful starting point for selecting one or more efficacious electrode combinations for patient 12. An electrode pattern may be determined to be clinically relevant by, e.g., a clinician, a manufacturer of IMD 14 or leads 16, or another source. In some examples, the clinical relevancy indicates that the electrode patterns are known to result in efficacious electrode combinations for at least some patients having a similar or identical patient condition as patient 12. Other selection parameters may be implemented instead of, or in addition to, the similarity in patient condition, to select the electrode patterns for the predetermined set of test electrode combination.

Figure 5A:
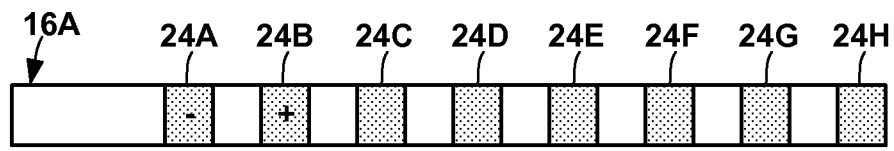
FIGS. 5A-5D are schematic diagrams illustrating an example group of electrode patterns present in a predefined set of electrode combinations.
Figure 5B:
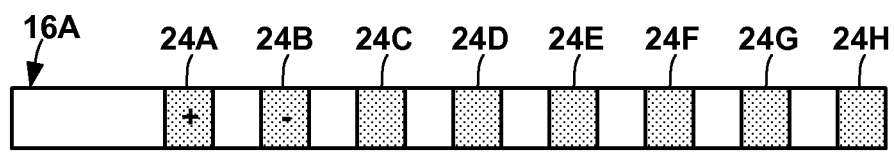
Figure 5C:
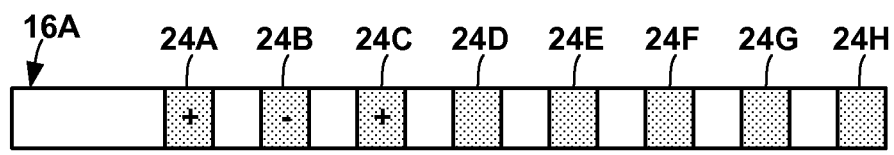
Figure 5D:
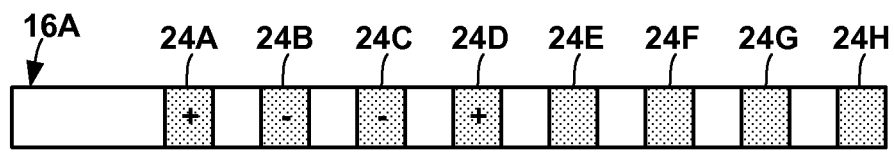

In one example, a predetermined group of test electrode patterns for testing on patient 12 includes four electrode patterns: a first simple bipole (e.g., as shown in the schematic diagram of FIG. 5A), a second simple bipole (e.g., as shown in the schematic diagram of FIG. 5B), a guarded cathode (e.g., as shown in the schematic diagram of FIG. 5C), and a guarded double cathode (e.g., as shown in the schematic diagram of FIG. 5D). These electrode patterns have been found to be clinically relevant for some patients that are candidates for SCS to treat pain. In other examples, other groups of electrode patterns can be used, which may include the same or different electrode patterns as those shown in FIGS. 5A-5D.

Returning again to the technique shown in FIG. 4A, processor 60 determines whether user input has been received via user interface 66 (82). Processor 60 may make this determination at any suitable time. For example, processor 60 may make this determination after controlling IMD 14 to deliver electrical stimulation to patient 12 with the selected electrode combination (80), or prior to, during, or after controlling IMD 14 to deliver electrical stimulation to patient 12 with the selected electrode combination (80).

Processor 60 may receive different types of user input during the delivery of test electrical stimulation according to a plurality of electrode combinations of a predefined set, and each type of user input may be associated with a respective responsive action (84). Examples of user inputs may include, for example, input marking an electrode combination, efficacy information, input requesting the automatic testing of the set of electrode combinations be paused, shifted backward, or slowed down, input requesting that certain electrode patterns or electrode combinations be eliminated from the set of test electrode combinations, or input requesting an electrode combination at a different axial position of lead 16A be tested (e.g., input selecting a start electrode combination at which the test electrical stimulation should be re-started).

In some examples, programmer 18 is configured such that a user may provide input selecting a different electrode combination in the set to "jump" to, but such that the user may not change the order of the electrode combinations in the set. As discussed above, the order of electrode combinations in the set is predetermined and selected to result in efficient transitions between subsequently tested electrode combinations.

In response to determining that user input has been received ("YES" branch of block 82), processor 60 may take an action responsive to the type of user input (84). For example, the user input may provide processor 60 with efficacy information that indicates the efficacy of electrical stimulation delivered via the selected electrode combination or another electrode combination. In response to receiving such user input, processor 60 may store the efficacy information in memory 62, along with an indication of the electrode combination to which the efficacy information relates. The electrode combination may be, for example, the electrode combination with which IMD 14 was delivering electrical stimulation to patient 12 when processor 60 received the efficacy information.

As another example, the user input may be input marking an efficacious electrode combination. The user may provide such input when, for example, patient 12 perceives efficacious electrical stimulation. In response to receive such user input, processor 60 may generate a marker (e.g., a flag, value, or other signal), associate the marker with the electrode combination with which IMD 14 was delivering electrical stimulation to patient 12 when the marker was received, and store the marker and associated electrode combination in memory 62 (or another memory).

In some examples, system 10 is configured such that a user may interrupt the automatic delivery of electrical stimulation to patient 12 via the set of electrode combinations, e.g., to pause the electrical stimulation or to change the position along lead 16A at which the electrode combinations are being tested (e.g., "jump" to a different position along lead 16A). Thus, in some examples, the user input received by processor 60 (82) may indicate that the electrode combination testing process should be paused (e.g., paused temporarily or stopped indefinitely). In response to receiving such user input, processor 60 may control IMD 14 to pause the delivery of electrical stimulation via the selected electrode combination. Processor 60 may, for example, transmit a control signal to processor 30 of IMD 14 via the respective telemetry modules 64, 40, and, in response to receiving the control signal, processor 30 of IMD 14 may control stimulation generator 34 to stop the delivery of electrical stimulation therapy to patient 12 via the selected electrode combination.

In some examples, user input that requests an electrode combination at a different axial position of lead 16A be tested may indicate a target axial position of lead 16A for the next tested electrode combination. For example, processor 60 may present a graphical representation of lead 16A, including electrodes 24, via a display of user interface 66 and the user may provide the input by interacting with the graphical representation of lead 16A. Processor 60 may, in some examples, indicate the electrode combination with which IMD 14 is currently delivering electrical stimulation to patient on the graphical representation of lead 16A. A user may provide input indicating the target axial position of lead 16A for the test electrical stimulation selected, e.g., by selecting a specific starting electrode 24 on the graphical representation of lead 16A and electrodes 24. The selected electrode may be, for example, the proximal-most or distal-most cathode electrode or anode electrode for the next tested electrode combination.

Depending on the implant site of lead 16A, different electrodes 24 of lead 16A may target different tissue sites. Thus, the user may provide input requesting that an electrode combination at a different axial position of lead 16A be tested if, for example, patient 12 or the clinician determines that a particular one or more electrodes 24 are not implanted proximate to a target tissue site in patient 12 and electrical stimulation therapy delivered via such electrodes may not be efficacious.

In response to receiving user input indicating that an electrode combination at a different axial position of lead 16A be tested, processor 60 may select a different electrode combination for testing on patient 12 and restart the technique shown in FIG. 4A. Processor 60 may, for example, select the next electrode combination in the predetermined order that is at the target axial position selected by the user. For example, processor 60 may select the next electrode combination in the set that includes any electrode at the axial position of lead 16A selected by the user, a proximal-most electrode at the selected axial position, or a distal-most electrode at the selected axial position of lead 16A.

Any combination of the aforementioned user inputs may be received by processor 60.

After taking the responsive action (84) or in response to determining no user input has been received ("NO" branch of block 82), processor 60 determines if there are additional electrode combinations in the set to test (86). In response to determining there are additional electrode combinations of the set to test ("YES" branch of block 86), processor 60 automatically selects a next electrode combination to test (88). The next electrode combination may be, for example, determined based on the predetermined order of the set of electrode combinations. As an example, the next electrode combination may be the electrode combination immediately following the previously tested electrode combination in the predetermined order. After selecting the next electrode combination to test, processor 60 may control IMD 14 to deliver electrical stimulation according to the next electrode combination (80).

In some examples of the technique shown in FIG. 4A, instead of sending separate control signals to IMD 14 for each tested electrode combination, processor 60 of programmer 18 may initiate an electrode combination identification process (in which a plurality of predetermined electrode combinations are tested in a predetermined order), and processor 30 of IMD 14 may control the automatic selection of the next electrode combination of the set in the predetermined order.

The electrode combinations of the set of electrode combinations are ordered such that transitions between subsequently tested electrode combinations are efficient. For example, as discussed above, adjacent electrode combinations in the order include at least one shared anode electrode or cathode electrode, which may help reduce the amount of time required to increase or decrease the intensity of electrical stimulation delivered via a particular electrode during a transition between electrode combinations.

Processor 30 may control stimulation generator 34 to shift between test electrode combinations using any suitable shifting technique. The shifting technique may be selected to minimize any discomfort to patient 12. For example, processor 30 may control the shifting of stimulation parameters smoothly from one electrode combination to a second electrode combination in a manner gradual enough to allow a user to intervene to adjust the stimulation intensity should the sensation become uncomfortable or imperceptible to patient 12 during the shifting process. In some examples, this gradual shifting is accomplished by reducing stimulation amplitude applied by one electrode combination and increasing stimulation amplitude applied by another electrode combination in a series of incremental steps to apply stimulation via the predefined sequence of different electrode patterns.

Processor 30 (or processor 60) may control the rate transition between electrode combinations based on instructions stored by memory 32 or received from programmer 18. For example, as described with respect to FIG. 4B, the rate of transition between electrode combinations may depend on the increments with which anodic and cathodic amplitudes are adjusted to shift between electrode combinations.

The amplitude adjustment increments may affect the duration of time required to shift between electrode combinations, and, therefore, the duration of time that electrical stimulation is delivered using a particular electrode combination. Thus, the minimum amplitude adjustment increments may be selected to increase or decrease the duration with which a particular electrode combination is tested on patient 12. Decreasing this value may increase the amount of time that a particular electrode combination is tested on patient 12, which may increase the amount of time patient 12 has to provide input regarding the efficacy of stimulation.

In some examples, the minimum amplitude adjustment increment and the rate of change, are preset by a manufacturer or distributor of programmer 18, IMD 14, or leads 16, and may not be modified by a user controlling the test electrical stimulation delivered to patient 12. For example, as described in further detail below with respect to FIGS. 10A-10D, in some examples, processor 60 (or another processor) adjusts the anodic and cathodic amplitudes in 10% amplitude increments, e.g., as defined by the steps in a predefined schedule of amplitude adjustments. In other examples, the amplitude adjustment increments may be 5% steps or 25% steps. In addition, for a particular predefined schedule, the amplitude adjustment increments may not all be the same size. For example, the amplitude adjustment increments could alternate between 4% and 6% as the steps propagate through the schedule.

In other examples, the minimum amplitude adjustment increment and the rate of change may be modified by a user. For example, the user may interact with user interface 66 of programmer 18 to modify the amplitude adjustment increments and/or the rate of change based on the particular patient 12 to which electrical stimulation is being delivered. Various factors, such as the sensitivity of the patient and the implant site of lead 16A, may affect the extent to which a particular patient perceives electrical stimulation. As a result, different patients may find different increment sizes to be comfortable. Thus, while electrode combinations are automatically tested in example techniques described herein, e.g., under the control of programmer 18, IMD 14, or both), some aspects of the electrode testing may be manually changed by a clinician.

After selecting the next electrode combination to test, processor 60 controls IMD 14 to deliver electrical stimulation with the selected electrode combination (80), determines whether user input has been received (82), and so forth until there are no further electrode combinations to test ("NO" branch of block 86).

In response to determining there are no additional electrode combinations to test ("NO" branch of block 86), the delivery of electrical stimulation via the set of electrode combinations in the predetermined order ends. In some examples, after processor 60 ends the electrical combination identification process, processor 60 generates and displays a list of the tested electrode combinations (e.g., the electrode combinations from the plurality of predetermined electrode combinations) for viewing by the clinician. The list can include, for example, graphical representations of the electrode combinations, names of the electrode combinations, or any other identifiers. Efficacy information associated with the electrode combinations, e.g., received by processor 60, may also be presented to the clinician (or other user). In this manner, programmer 18 may present information to the clinician (or other user) that informs the identification of an efficacious electrode combination for patient 12.

For example, the efficacy information may be displayed alongside the associated electrode combination identifier, or the user interface generated by processor 60 may be dynamic and a user may interact with the user interface to select an electrode combination from the list, and, in response to receiving the user input, processor 60 can retrieve the efficacy information associated with the selected electrode combination, e.g., from memory 62, and display the efficacy information via a display of user interface 66. In some examples, processor 60 may order the list of tested electrode combinations based on the efficacy information, e.g., an ascending or descending order of efficacy ratings.

Processor 60 of programmer 18, automatically or with the aid of a clinician, may select one or more of the tested electrode combinations based on the results of the electrical stimulation delivery via the plurality of test electrode combinations. Processor 60 may, for example, select one or more of the electrode combinations and create one or more therapy programs (including the selected electrode combinations) for programming IMD 14 for chronic therapy delivery or for further testing, or take any other suitable action.

In some examples, processor 60 of programmer 18, automatically or with the aid of a clinician, may select additional electrode combinations to test on patient 12 based on the results of the electrical stimulation delivery via the plurality of test electrode combinations. Processor 60 may select the additional electrode combinations to test on patient 12 using any suitable technique. In some examples, processor 60 selects electrode combinations, e.g., associated with the highest efficacy ratings, from the plurality of tested electrode combinations, and the selected electrode combinations can be used to determine additional combinations to test, e.g., using an electrode combination search algorithm, a table, or another technique.

An example search algorithm is described in U.S. Patent Application Publication No. 2005/0060009 by Goetz et al., which is entitled, "SELECTION OF NEUROSTIMULATOR PARAMETER CONFIGURATIONS USING GENETIC ALGORITHMS" and published on Mar. 17, 2005. U.S. Patent Application Publication No. 2005/0060009 by Goetz et al. describes devices, systems, and techniques for selection of parameter configurations, including electrode combinations, using genetic algorithms, which may provide guidance in the electrode combination selection process, interactively guiding the clinician by suggesting electrode combination that are most likely to be efficacious given the results of tests already performed during an evaluation session (e.g., tests performed using the set of electrode combinations). U.S. Patent Application Publication No. 2005/0060009 by Goetz et al. is incorporated herein by reference in its entirety.

As another example of how additional electrode combinations to test on patient 12 may be selected, processor 60 may select one or more of the electrode combinations from the set of tested electrode combinations, and the selected one or more electrode combinations may indicate that certain other electrode combinations may be efficacious. For example, a selected electrode combination may be associated with one or more additional electrode combinations in a table stored by memory 62 (or another memory, such as memory 32 of IMD 14). The one or more additional electrode combinations can be, for example, electrode combinations that may result in similar therapy fields as the one or more electrode combinations selected from the set, or electrode combinations that are known to result in similar efficacy based on historical data from another patient or class of patients. A therapy field can be, for example, an electrical field model that is generated based upon a patient anatomy data (specific to patient 12 or generic to multiple patients) and a therapy program defining stimulation parameter values (including an electrode combination), where the electrical field model represents the areas of a patient anatomical region that will be covered by an electrical field during therapy delivery via the associated electrode combination.

Figure 4B:
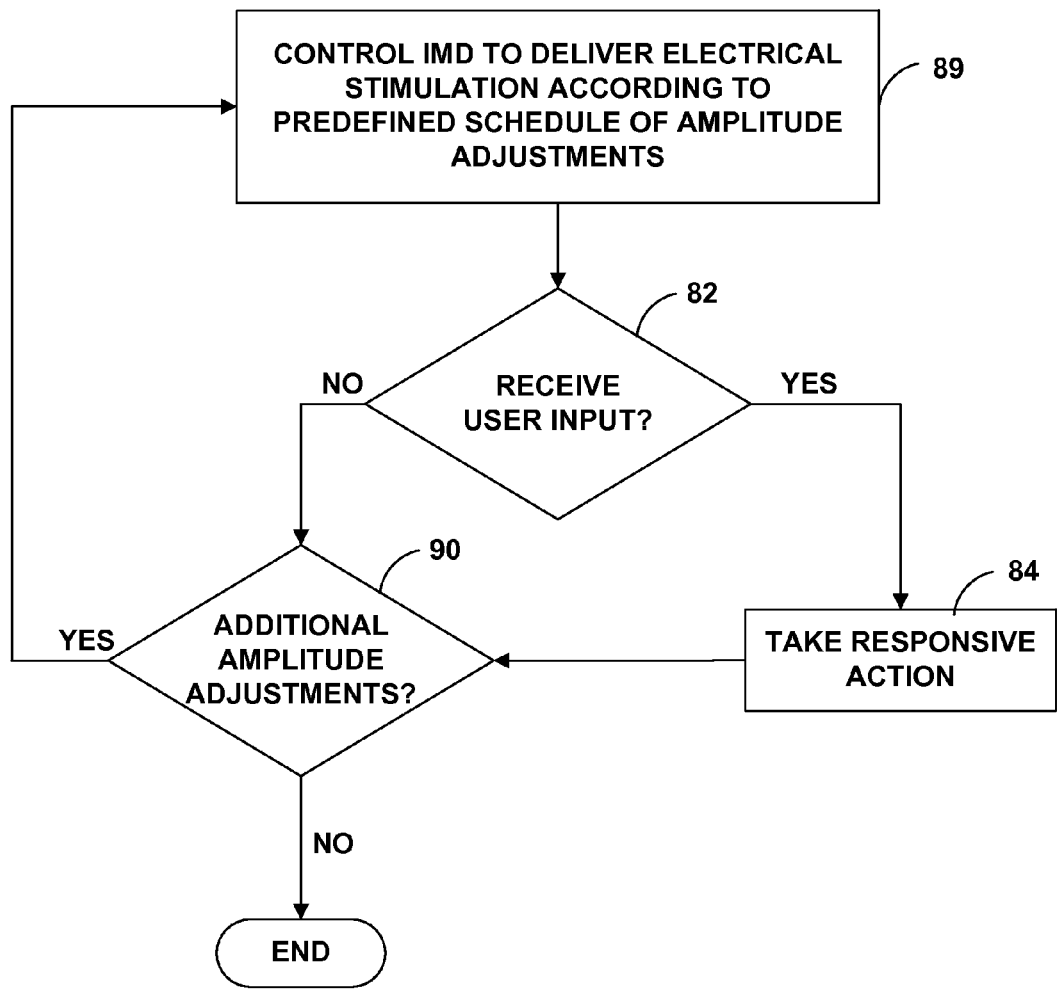

FIG. 4B is a flow diagram of another example technique for identifying one or more electrode combinations that may provide efficacious therapy for patient 12. In the technique shown in FIG. 4B, processor 30, e.g., under the control of processor 60 of programmer 18, controls stimulation generator 34 to deliver electrical stimulation therapy to patient 12 according to a predefined schedule of amplitude adjustments (89). The predefined schedule of amplitude adjustments defines the set of electrode combinations to be automatically tested on patient 12, e.g., during a programming session. The predefined schedule of amplitude adjustments may be stored by memory 62 of programmer 18, memory 32 of IMD 14, or a memory of another device (e.g., a cloud memory device).

The predefined schedule of amplitude adjustments includes a plurality of steps and, for each step, the active electrodes used for delivery of electrical stimulation therapy, and, for each of the active electrodes, the anodic and cathodic amplitude settings. Each "step" may represent, for example, a time slot, such that subsequent steps are taken in subsequent slots of time. In some examples, the time slot is predefined, and may be, for example, 200 milliseconds (ms) to about 1 second. During a particular time slot, an electrode combination (defined by the active electrodes) and respective anodic and cathodic amplitude settings with which IMD 14 delivers electrical stimulation to patient 12 remains substantially the same (e.g., nearly the same or the same).

In some examples in which stimulation generator 34 and stimulation generator 34 include a plurality of stimulation engines, processor 30 may determine an absolute current amplitude value for the electrode combination, a percentage contribution of the absolute current amplitude for each anode in the electrode combination (the anodic amplitude), and an effective amplitude for each cathode in the electrode combination (the cathodic amplitude). Processor 60 may control stimulation generator 34 to incrementally increase or decrease the anodic amplitude and cathodic amplitudes (based on the amplitude settings defined by the schedule) in any suitable amplitude adjustment increments, which can be, but need not be, the same for all of the steps of the schedule. For example, the amplitude adjustment increments may be defined as a percent change, and the anodic and/or cathodic amplitude may be, modified (e.g., increased or decreased) by processor 60 in any suitable percentage increments, such as about 4%, 5%, 6%, 10%, or 25% increments. While the total amplitude of the electrical stimulation may not change with the amplitude adjustments, the distribution of the amplitude between the anodes and/or between the cathodes changes with each amplitude adjustment defined by the schedule.

The amplitude adjustment increments may be selected to minimize the perception of the electrode combination transition by patient 12. In some examples, the schedule defines cathodic amplitude settings as amplitude values, such that the minimum amplitude adjustment increment for a cathodic amplitude may be defined in terms of amplitude value. In some examples, the minimum amplitude adjustments can be about 1/64 of 0.1 milliamps (mA), such as about 1 microamp (μA), to about 0.1 mA. In addition, in some examples, the schedule defines anodic amplitude settings as a percentage of total current, such that the minimum amplitude adjustment increment for anodic amplitude may be defined in terms of a percentage increment. In one example, the percentage increments may be, for example, about 4% to about 6% each.

In some examples, stimulation generator 34 adjusts the anodic and cathodic amplitudes using the same amplitude adjustment increments. In other examples, the stimulation generator 34 adjusts the anodic and cathodic amplitudes using different amplitude adjustment increments. In some examples, the schedule may define the amplitude adjustment increments, e.g., by defining the anodic and cathodic amplitudes for each step.

The technique shown in FIG. 4B is similar to the technique described with respect to FIG. 4A, but instead of determining whether there are additional electrode combinations to test (86) and selecting the next electrode combination to test (88), processor 60 automatically selects a next electrode combination in the set to test as a result of incrementally adjusting anodic and/or cathodic currents in accordance with a predefined schedule of amplitude adjustments. A shift between adjacent electrode combinations in the predefined set (referred to herein as "first" and "second" electrode combinations for ease of description) may occur due to the incremental amplitude adjustment defined by a step of the schedule.

As described in further detail with respect to FIGS. 10A-11D, processor 30 may control stimulation generator 34 to shift between first and second electrode combinations, in accordance with the schedule, by at least incrementally decreasing the current amplitude sunk by cathodes of a first electrode combination that are not shared by the second electrode combination, and incrementally increasing the current amplitude sunk by the cathodes of the second electrode combination that are not shared with the first electrode combination until only cathodes of the second electrode combination are active. If the second electrode combination includes at least one more cathode than the first electrode combination, then stimulation generator 34 may incrementally decrease the current amplitude sunk by cathodes shared by the first and second electrode combinations as stimulation generator 34 incrementally decreases the current amplitude sunk by the other cathodes of the first electrode combination and incrementally increases the current amplitude sunk by the other cathodes of the second electrode combination. If the second electrode combination includes at least one fewer cathode than the first electrode combination, then stimulation generator 34 may incrementally increase the current amplitude sunk by cathodes shared by the first and second electrode combinations as stimulation generator 34 incrementally decreases the current amplitude sunk by the other cathodes of the first electrode combination and incrementally increases the current amplitude sunk by the other cathodes of the second electrode combination.

In some examples, processor 30 may control stimulation generator 34 to shift between first and second electrode combinations, in accordance with the schedule, by at least incrementally decreasing a percentage of current assigned to (e.g., sourced by) anodes of the first electrode combination that do not overlap with the second electrode combination, and incrementally increasing a percentage of current assigned to anodes of the second electrode combination that do not overlap with the first electrode combination until only anodes of the second electrode combination are active. If the second electrode combination includes at least one more anode than the first electrode combination, then stimulation generator 34 may incrementally decrease the percentage of current assigned to anodes shared by the first and second electrode combinations as stimulation generator 34 incrementally decreases the percentage of current assigned to the other anodes of the first electrode combination and incrementally increases the percentage of current assigned to other anodes of the second electrode combination. If the second electrode combination includes at least one fewer anode than the first electrode combination, then stimulation generator 34 may incrementally increase the percentage of current assigned to anodes shared by the first and second electrode combinations as stimulation generator 34 incrementally decreases the percentage of current assigned to the other anodes of the first electrode combination and incrementally increases the percentage of current assigned to other anodes of the second electrode combination.

The transition between the first and second electrode combinations in the predefined set may occur once only cathodes and anodes of the second electrode combination are active. The amplitude adjustment settings and steps of the schedule may define the rate of transition between electrode combinations. In some examples, a clinician may provide input to processor 60 via user interface 66 to modify the amplitude adjustment increments (e.g., select an increment within a preset range), which may, in turn, affect the rate of transition between electrode combinations. Thus, in some examples, the testing of a set of electrode combinations may be automated by programmer 18, but certain aspects of the testing may be controlled by a user.

As shown in the example of FIG. 4B, if processor 60 has not received user input ("NO" branch of block 82) or after taking a responsive action (84), processor 60 may determine whether the schedule defines any additional (anodic and cathodic) amplitude adjustments to be made (90). For example, processor 60 may determine whether the schedule includes any steps that have not been completed yet. In response to determining there are additional amplitude adjustments to be made ("YES" branch of block 90), processor 60 may continue controlling IMD 14 to deliver electrical stimulation to patient 12 with the electrode combinations and respective anodic and cathodic amplitudes defined by the predefined schedule (80). In response to determining there are no additional amplitude adjustments to implement ("NO" branch of block 90), processor 60 may terminate the automatic testing of the predefined set of electrode combinations.

FIG. 6 is a table illustrating an example set of test electrode combinations that may be used to identify one or more efficacious electrode combinations for patient 12 in accordance with some example techniques described herein. As discussed in further detail below, the set of test electrode combinations are arranged in a predetermined order that has been determined to result in efficient transitions between adjacent electrode combinations. The set of test electrode combinations shown in FIG. 6 may be stored by memory 32 of IMD 14, memory 62 of programmer 18, or a memory of another device.

Electrodes 24 of lead 16A are shown in the first column of the table shown in FIG. 6, and the other columns indicate electrode combinations. The top row shown in FIG. 6 includes identifiers for the electrode combinations, i.e., "A," "B," and so forth through "EE." The alpha-identifiers shown in FIG. 6 are merely an example of an identifier, and any suitable identifier, whether any combination of alphabetical, numeric, graphical, and the like, may be associated with stored electrode combinations and used to identify the stored electrode combination. Each of the other rows in the table shown in FIG. 6 corresponds to a respective electrode. For each electrode combination A-EE, a symbol, "+" (indicating an anode) or "−" (indicating a cathode) in the row corresponding to the electrode indicates the electrode is active and included in the electrode combination. For example, as shown in FIG. 6, electrode combination A includes electrodes 24A, 24B, where electrode 24A serves as a cathode and electrode 24B serves as an anode.

In some example techniques for identifying one or more efficacious electrode combinations, processor 60 of programmer 18 or processor 30 of IMD 14 or another device controls stimulation generator 34 (FIG. 2) of IMD 14 to generate and deliver electrical stimulation to patient 12 via each of electrode combinations A-EE shown in FIG. 6. Scanning through each of electrode combinations A-EE may take, for example, less than five minutes, such as about three minutes, if the scanning is uninterrupted. A technique in which processor 60 of programmer 18 controls stimulation generator 34 is described with reference to FIG. 6. In other examples, however, processor 30 of IMD 14 or another device may perform any part of the technique described herein.

Processor 60 is configured to control stimulation generator 34 to generate and deliver electrical stimulation to patient 12 via each of electrode combinations A-EE at different times. For example, processor 60 may transmit control signals to IMD 14 that cause stimulation generator 34 (e.g., under the control of processor 30) to generate and deliver electrical stimulation via electrode combination A, and, subsequently, terminate the delivery of electrical stimulation via electrode combination A and deliver electrical stimulation via electrode combination B, and, subsequently, deliver electrical stimulation via electrode combination A, and, subsequently, terminate the delivery of electrical stimulation via electrode combination B and deliver electrical stimulation via electrode combination C, and so forth until each of electrode combinations A-EE has been tested. As described with respect to FIGS. 10A-11D, the transitions between electrode combinations A-EE may be relatively subtle due to the manner in which the cathodic and anodic amplitudes may be adjusted to transition between electrode combinations.

In some examples, stimulation generator 34 may generate the electrical stimulation signal delivered via each of the electrode combinations A-EE with a common set of other stimulation parameter values (e.g., current or voltage amplitude and frequency). In this way, the variable that is changing may be limited to the electrodes with which electrical stimulation is delivered to patient 12. In other examples, however, stimulation generator 34 may generate the electrical stimulation signal delivered via at least two of the electrode combinations A-EE with different stimulation parameter values. Different stimulation parameter values may be selected if, for example, one set of other stimulation parameter values would result in uncomfortable stimulation for one or more of the electrode combinations due to the relative position between the electrodes of the electrode combination and the tissue of patient 12.

In accordance with an example automated electrode combination testing technique, under the control of processor 60, stimulation generator 34 may generate and deliver electrical stimulation therapy to patient 12 via electrode combination A. Under the control of processor 60, stimulation generator 34 may, for example, initiate electrical stimulation via electrode combination A by assigning 100% of the amplitude to cathode electrode 24A and 100% of the amplitude to anode electrode 24B. Stimulation generator 34 may deliver electrical stimulation via electrode combination A for a predetermined period of time sufficient for patient 12 to feel the effects of the electrical stimulation. The predetermined period of time during which IMD 14 delivers electrical stimulation to patient 12 via a particular electrode combination may be referred to as a "test period."

The duration of the test period may differ between patients, based on clinician preference, or based on other factors. In addition, the duration of the test period may depend on the number of anodic and cathodic amplitude adjustment increments between adjacent electrode combinations. In some examples, the test period may be 0.2 seconds to about 10 seconds. Within a test period for a particular electrode combination, stimulation generator 34 may change the anodic and cathodic amplitudes. Depending on the amplitude adjustment increments, stimulation generator 34 may deliver electrical stimulation to patient 12 according to a particular electrode combination and particular anodic and cathodic amplitude setting for about 200 ms to about 1 second. This time period may be a predetermined period of time sufficient for patient 12 to feel the effects of the electrical stimulation.

In some examples, the test period may be extended, e.g., if the automatic scanning implemented by programmer 18 is paused by a clinician and the electrical stimulation according to a particular electrode combination is maintained while a user adjusts one or more stimulation parameter values, e.g., as discussed above with respect to FIGS. 4A and 4B, and in further detail below with respect to FIG. 12.

After the test period for electrode combination A, under the control of processor 30, stimulation generator 34 may generate and deliver electrical stimulation therapy to patient 12 via electrode combination B for a test period. Stimulation generator 34 may shift from electrode combination A to electrode combination B using any of the techniques described herein. As shown in FIG. 6, cathode electrode 24A and anode electrode 24B are shared by (common to) electrode combinations A and B. However, electrode combination B includes another anode electrode 24C. Thus, in one example, processor 30 controls stimulation generator 34 to gradually increase the amplitude sourced by anode electrode 24C, e.g., in predetermined minimum amplitude increments, while gradually decreasing the amplitude applied to anode electrode 24B. The delivery of electrical stimulation is transitioned from electrode combination A to electrode combination B at the point in time at which anode electrode 24C was activated.

Similarly, as described with respect to FIGS. 10A-11D, stimulation generator 34 may continue to gradually increase the amplitude sourced by anode electrode 24C, while gradually decreasing the amplitude applied to anode electrode 24B until anode electrode 24B is deactivated. At this time, the shift from electrode combination B to electrode combination C is complete. During the increasing of the anodic current assigned to anode electrode 24C and the decreasing of the anodic current assigned to anode electrode 24C, electrode combination B is being tested on patient 12.

Processor 30 or processor 60 controls the order in which the electrode combinations A-EE are selected and tested on patient 12 based on the predetermined order in which the electrode combinations are stored and arranged in the table shown in FIG. 6. Thus, in the example shown in FIG. 6, after delivering electrical stimulation therapy to patient 12 via electrode combination B for a test period, stimulation generator 34 may generate and deliver electrical stimulation therapy to patient 12 via electrode combination C for a test period. After delivering electrical stimulation therapy to patient 12 via electrode combination C for a test period, stimulation generator 34 may generate and deliver electrical stimulation therapy to patient 12 via electrode combination D for a test period, followed by electrode combination E for a test period, and so forth until stimulation generator 34 delivers electrical stimulation to patient 12 via each of electrode combinations A-EE shown in FIG. 6.

The test periods during which electrode combinations A-EE are each tested may be substantially the same (e.g., the same or nearly the same) or different, which may depend on the increments with which the anodic and cathodic amplitudes are adjusted, as discussed above and/or whether user input interrupting the delivery of stimulation is received by processor 60 of programmer 18. The user input may cause a test period to be restarted in some examples.

The electrode combinations in the set shown in FIG. 6 are arranged to define a sequence of major electrode patterns, which, in the example shown in FIG. 6, are the four electrode patterns shown in FIGS. 5A-5D. Each of the electrode patterns shown in FIGS. 5A-5D appear at multiple times at different positions in the sequence. For example, the simple bipole shown in FIG. 5A is used to define electrode combinations A, E, I, M, Q, and Y. In this way, the major electrode patterns are tested at different axial positions along lead 16A, which may increase the robustness of the process for identifying an efficacious electrode combination for patient 12.

In addition, the electrode combinations in the set shown in FIG. 6 include minor electrode patterns. For example, electrode combination B includes two anodes 24B, 24C, which is an electrode pattern that results when stimulation generator 34 is transitioning from delivery of electrical stimulation via electrode combination A to delivery of electrical stimulation via electrode combination C. Other minor electrode patterns that appear in the set of electrode combinations shown in FIG. 6 include electrode combinations D, X, BB, and DD.

The electrode patterns are arranged in the sequence such that the transition between subsequently tested electrode combinations is logical and efficient. In some examples, the logic and efficiency is at least partially attributable to the arrangement of electrode combinations in the set such that adjacent electrode combinations include at least one anode electrode or cathode electrodes. For example, electrode combination K includes anode electrode 24B and cathode electrode 24C from immediately preceding electrode combination J. As another example, electrode combination T includes anode electrode 24D and cathode electrode 24E from immediately preceding electrode combination S. Sharing at least one anode or cathode electrode with a prior-tested electrode combination may reduce the amount of time required to gradually modify amplitude delivered via a particular electrode.

As discussed above, in some examples, a plurality of electrode combinations in a set to be tested on patient 12 may be arranged in a predetermined order such that the electrode combinations move through the levels of electrodes 24 (e.g., "walked" down lead 16A). For example, when electrode combinations A-EE are selected in the predetermined order shown in FIG. 6, the electrodes with which electrical stimulation is delivered to patient 12 move distally down lead 16A (where electrode 24H is a distal-most electrode). For at least some electrode combinations, a distal-most electrode (e.g., the electrode closest to a distal end of lead 16A) is more distal (e.g., closer to a distal end of lead 16A) than the proximal-most electrode of the previous electrode combination in the set. For example, in the set of electrode combinations shown in FIG. 6, a distal-most electrode of electrode combination B is electrode 24C, which is closer to a distal end of lead 16B than proximal-most electrode 24A of electrode combination B.

As another example of how electrode combinations may be ordered to move through the levels of electrodes 24, the electrode combinations may be ordered such that, with the exception of the first two electrode combinations, a distal-most electrode of a particular electrode combination (referred to as a "first" electrode combination for ease of description) is closer to a distal end of lead 16A than the proximal-most electrode of a preceding electrode combination (referred to as a "second" electrode combination for ease of description) that is separated (in the order) from the first electrode combination by one or more electrode combinations. For example, in the set of electrode combinations shown in FIG. 6, a distal-most electrode 24E of electrode combination L is closer to a distal end of lead 16A than proximal-most electrode 24B of electrode combination J (which precedes combination L in the order and is separated from combination L by at least one electrode combination).

IMD 14, programmer 18, or another device may store a set of electrode combinations (e.g., the set shown in FIG. 6 including electrode combination A-EE) for automatically testing on patient 12 in order to identify an efficacious electrode combination for patient 12. In some examples, IMD 14, e.g., independently or under the control of programmer 18 or another device, automatically delivers electrical stimulation to patient 12 according to each electrode combination of the set and a user may not modify the electrode combinations in the set. This may be, for example, because a clinician has determined that it is valuable to test each electrode combination in the set on patient 12 in order to be thorough. In other examples, however, as discussed above with respect to FIGS. 4A and 4B, a user may modify the electrode combinations in the set, e.g., by eliminating certain electrode combinations. A clinician may, for example, eliminate electrode combinations that include electrodes that the clinician has determined are not proximate a target tissue site in patient 12, and, therefore, may not result in efficacious therapy delivery to patient 12.

A user may modify electrode combinations in the set using any suitable technique. For example, programmer 18 may generate a display that lists the electrode combinations in the set and a clinician may, with the aid of user interface 66 (FIG. 3), manually select and remove electrode combinations from the set by identifying the electrode combinations by the associated identifier (e.g., "A," "B", etc.). In addition, or instead, programmer 18 may generate a display that lists the electrode patterns that are used to define the electrode combination, and a clinician may, with the aid of user interface 66 (FIG. 3), manually select and remove electrode patterns being tested by identifying the electrode combinations by the associated identifier (e.g., "A," "B", etc.). In response to receiving such user input, processor 60 of programmer 18 (or another processor, such as processor 30 of IMD 14) may determine which electrode combinations of the set include the electrode pattern and eliminate the determined electrode combinations from the set. For example, in response to receiving user input that indicates a guarded double cathode should be removed from the set of electrode combinations being tested on patient 12, processor 60 may eliminate electrode combinations H, L, P, and T from the set of electrode combinations to be tested on patient 12.

In addition, or instead of the examples discussed above, a user may eliminate electrode combinations in the set by interacting with user interface 66 to provide select a starting electrode for the testing process. The starting electrode may be, for example, a proximal-most cathode electrode for the first electrode combination (or a distal-most cathode electrode, depending on the order in which electrode combinations are "walked" down lead 16A). In response to receiving the user input, processor 60 of programmer 18 (or another processor, such as processor 30 of IMD 14) may determine which electrode combinations of the set include proximal-most cathode electrode (or distal-most cathode electrode in other examples) and skip to that part of the set. For example, in response to receiving user input that indicates the electrode testing should start with electrode 24C as the proximal-most cathode, and the electrode combinations are walked down lead 16A toward the distal end of lead 16A, processor 60 may begin the testing at electrode combination I.

In addition, or instead of the examples discussed above, a user may eliminate electrode combinations in the set by interacting with user interface 66 to provide select an ending electrode for the testing process. The ending electrode may be, for example, a distal-most electrode (e.g., cathode electrode) for the first electrode combination (or a proximal-most electrode, depending on the order in which electrode combinations are "walked" down lead 16A). In response to receiving the user input, processor 60 of programmer 18 (or another processor, such as processor 30 of IMD 14) may determine which electrode combinations of the set include distal-most electrodes (or distal-most electrode in other examples) that are distal to the electrode selected by the user and eliminate the determined electrode combinations from the set. For example, in response to receiving user input that indicates the electrode testing should end at electrode 24G and the electrode combinations are walked down lead 16A toward the distal end of lead 16A, processor 60 may eliminate electrode combinations BB-EE from the set of electrode combinations to be tested on patient 12. The testing of electrical combinations may be driven by cathodes, so, in some examples, in response to receiving user input indicating the user wants to end the testing at electrode 24G, processor 60 ends the testing with the electrode combination in the set having electrode 24G as a distal-most cathode.

Combinations that include anode electrodes distal to electrode 24G may still be tested in response to the user input indicating 24G should be the last cathode electrode tested. One exception, however, maybe if processor 60 determines, e.g., based on a measured impedance greater than a threshold value, that the electrical pathway including electrode 24H (or another electrode) has an open circuit condition. In this case, processor 60 may automatically skip every electrode combination that includes that high impedance electrode as an active electrode. Processor 60 may, in some examples, notify a user via user interface 66 that the electrode combinations were skipped, that a particular electrode has been identified as exhibiting a high impedance, or both.

In addition, or instead of the examples discussed above, a user may determine that skipping an area of stimulation is desirable. Thus, the user may provide input to, for example, eliminate a particular electrode 24C from the electrode combinations being tested. For example, if the user indicates electrode 24C should be eliminated because it does not provide a desirable outcome when programmed as a cathode, processor 60 can skip electrode combinations H-L from the predefined set of electrode combinations. In any of these examples in which electrode combinations are skipped, processor 60 may control stimulation generator 34 to gradually apply the next electrode combination in the step, e.g., using the techniques to ramp up or ramp down anodic and cathodic amplitudes described herein. For example, processor 60 may control stimulation generator 34 to ramp down electrical stimulation applied via one electrode combination to a zero amplitude (or as close to zero as the hardware permits) prior to ramping up electrical stimulation applied via the next electrode combination selected based on the user input. This technique may help minimize any sudden changes in electrical stimulation that may be uncomfortable to patient 12.

Other techniques may be used to modify the electrode combinations of a predetermined set of electrode combinations to be tested on patient 12. In some examples in which the electrode combinations in the set are ordered such that the electrode combinations move through the levels of electrodes 24 (e.g., "walked" down lead 16A) in a common direction, the modification to the electrode combinations of the set of electrode combinations does not change the general order of electrode combinations, such that the modified set also includes electrode combinations arranged in order such that the electrode combinations move through the levels of electrodes.

In some examples, system 10 may be configured to enable the user to modify electrode combinations in the set at any suitable time. For example, programmer 18 can be configured to enable the user to modify electrode combinations in the set prior to initiating the test therapy delivery according to the set of test electrode combinations. In addition, or instead, a user may modify electrode combinations in the set during the test therapy delivery according to the set of test electrode combinations. For example, the user may pause the automatic scanning any time after initiating the test therapy delivery according to the set of test electrode combinations, eliminate some electrode combinations, and then control IMD 14 to resume delivery of the test electrical stimulation via the remaining electrode combinations in the set.

While lead 16A including one column of eight electrodes is primarily referred to throughout the description of the electrode combination identification techniques described above, the techniques described herein may also be used to identify one or more efficacious electrode combinations that include a subset of electrodes of a lead having a greater or a fewer number of electrodes, or even two or more columns of electrodes.

In another example, a set of electrode combinations includes only electrode combinations in which the anode and cathode electrodes are programmed together on adjacent electrodes without any inactive electrodes between the active electrodes. This type of arrangement of anode and cathode electrodes may minimize the area of activation of the neurons as the electrode combinations propagate down the electrode array. Thus, in some examples, a predefined set of electrode combinations is similar to that shown in FIG. 6, but does not include electrode combinations C and CC.

FIGS. 7-9 are tables illustrating example sets of test electrode combinations that may be used to identify one or more efficacious electrode combinations for patient 12 in accordance with some example techniques described herein. The set of test electrode combinations shown in FIG. 7 may be used to identify one or more efficacious electrode combinations that include a subset of electrodes of a lead having six electrodes, i.e., electrodes E0-E5, where electrode E5 may be closer to a distal end of the lead than electrode E0 or vice versa. The set of test electrode combinations shown in FIG. 8 may be used to identify one or more efficacious electrode combinations that include a subset of electrodes of a lead having four electrodes, i.e., electrodes E0-E3, where electrode E3 may be closer to a distal end of the lead than electrode E0 or vice versa. The set of test electrode combinations shown in FIG. 9 may be used to identify one or more efficacious electrode combinations that include a subset of electrodes of a lead having five electrodes, i.e., electrodes E0-E4, where electrode E4 may be closer to a distal end of the lead than electrode E0 or vice versa.

The electrode combinations in each of the sets of test electrode combinations shown in FIGS. 7-9 are arranged to define a sequence of major electrode patterns, which are the four electrode patterns shown in FIGS. 5A-5D. In addition, as with the set of electrode combinations shown in FIG. 6, the electrode combinations in the sets shown in FIGS. 7-9 include minor electrode patterns.

As with the set of test electrode combinations shown in FIG. 6, each of the sets of test electrode combinations shown in FIGS. 7-9 are arranged in a predetermined order that has been determined to result in efficient transitions between adjacent electrode combinations. For example, within each set, adjacent electrode combination includes at least one shared anode electrode or cathode electrode. In addition, within each set, the order of electrode combinations results in electrode combinations being walked down the lead (e.g., from a proximal end to a distal end, or vice versa).

Other sets of electrode combinations are contemplated and may depend on the electrode patterns that are selected to be tested on patient, the number of electrodes available for defining the electrode combinations, and the like.

In some examples, the anodic amplitudes and cathodic amplitudes are adjusted in a predetermined manner as the electrode combinations of a predefined set are tested in a predetermined order. The predetermined manner may be selected such that one or more electrode combinations of the predefined set are delivered with different combinations of anodic and cathodic amplitudes. Processor 60 of programmer 18 (or another device, such as processor 30 of IMD 14) may control the adjustment to the anodic amplitudes and cathodic amplitudes in a predetermined manner using a predefined schedule of amplitude adjustments, which defines the set of electrode combinations to be automatically tested on patient 12, e.g., during a programming session, which defines the set of electrode combinations to be automatically tested on patient 12, e.g., during a programming session FIGS. 10A-10D illustrate an example predefined schedule of amplitude adjustments. The predefined schedule shown in FIGS. 10A-10D includes the electrode combinations A-EE described with respect to FIG. 6. However, in addition to indicating which electrodes are active and the polarity of the electrodes, the schedule includes the anodic and cathodic amplitude settings for each time slot. The predefined schedule of amplitude adjustments includes a plurality of steps, which are numbered in the leftmost column of the table shown in FIGS. 10A-10D, and, for each step, the active electrodes used for delivery of electrical stimulation therapy, and, for each of the active electrodes, the anodic and cathodic amplitude settings. The settings are expressed in terms of percentages of total anodic amplitudes (shown as positive percentages) and cathodic amplitudes (shown as negative percentages).

Each "step" may represent, for example, a time slot. When implementing the electrode testing process using the schedule shown in FIGS. 10A-10D, processor 60 may control stimulation generator 34 of IMD 14 (e.g., directly or indirectly via instructions sent to processor 30 of IMD 14) to deliver electrical stimulation to patient 12 according to the active electrodes and amplitude settings of step 1, followed by step 2, and so forth until the end of the schedule is reached. At that time, the automatic scanning through a predefined set of electrode combinations may be complete. Each step may represent a time slot, such that steps 1-151 represent consecutive time slots. In some examples, the time slot is predefined, and may be, for example, 200 ms to about 1 second, and may be adjusted by a user. During a particular time slot, the electrode combination and respective anodic and cathodic amplitude settings with which IMD 14 delivers electrical stimulation to patient 12 remains substantially the same, as defined by the particular step.

As shown in FIG. 10A, for example, when implementing the electrode testing process using the schedule shown in FIGS. 10A-10D, processor 30 may control stimulation generator 34 of IMD 14 (e.g., directly or indirectly via instructions received from processor 60 of programmer 18) to begin the electrode combination testing process by delivering electrical stimulation to patient 12 according to electrode combination A for a time slot, wherein 100% of the electrical stimulation current (or voltage if IMD 14 is a voltage controlled device) is sunk by cathode electrode 24A and 100% of the stimulation is sourced by anode electrode 24B. In a next time slot, i.e., step 2, processor 30 controls stimulation generator 34 to decrease the current sourced by anode electrode 24B by an increment of 10% of the total anodic amplitude, and increase the current sourced by anode electrode 24C by an increment of 10% of the total anodic amplitude, while the cathodic amplitude assigned to electrode 24A is held at 100%. This amplitude adjustment results in a transition from electrode combination A to electrode combination B.

In a next time slot, i.e., step 3, processor 30 controls stimulation generator 34 to decrease the current sourced by anode electrode 24B by another increment of 10% of the total anodic amplitude, and increase the current sourced by anode electrode 24C by another increment of 10% of the total anodic amplitude. This gradual modification to the anodic amplitude continues, and, as a result, at time slot 11, the electrode combination is transitioned from electrode combination B to electrode combination C. Steps 2-10 represent the test period for electrode combination B.

The transition between adjacent electrode combinations is relatively subtle (e.g., in perception by patient 12) due to the incremental modifications in anodic and/or cathodic amplitudes used to achieve the transition. This may help minimize discomfort to patient 12 resulting from the transitions in electrode combinations.

As shown, a plurality of electrode combinations (i.e., electrode combinations B-D, F, H, J-L, N, P, R, T, V, X, Z, BB, and DD) are tested using a plurality of different anodic amplitude settings. The electrode combinations and respective amplitude settings are shown as "sub-combinations" in the table of FIGS. 10A-10D, e.g., B1-B9. The efficacy of electrical stimulation delivered via some electrode combinations may change depending on the anodic and cathodic amplitude settings. Thus, the schedule shown in FIGS. 10A-10D may be useful for more thoroughly evaluating an electrode combination compared to techniques in which every electrode combination is only tested at a one anodic and cathodic amplitude setting. The electrode combinations A, E, G, I, M, O, Q, S, U, W, Y, AA, CC, and EE only have possible one anodic and cathodic amplitude setting (for a particular stimulation amplitude) because of the presence of only one anode electrode and one cathode electrode.

The schedule shown in FIGS. 10A-10D may be useful for efficiently evaluating a plurality of electrode combinations at a plurality of different anodic and cathodic amplitude settings. When the schedule shown in FIGS. 10A-10D or a similar schedule is stored and implemented by processor 60 (or processor 30) to test a predefined set of electrode combinations on patient 12, the anodic and cathodic amplitude settings and the timeline for modifying the anodic and cathodic amplitude settings is also defined and arranged in a manner that results in an efficient use of time. This may help minimize or even eliminate the clinician control required to evaluate a plurality of electrode combinations at a plurality of different anodic and cathodic amplitude settings.

A predefined schedule of amplitude adjustments stored by IMD 14, programmer 18, or another device may define the anodic and cathodic amplitude settings using any suitable convention. In FIGS. 10A-10D, for example, the settings are stored as percentages of the total anodic amplitude and total cathodic amplitude. FIGS. 11A-11D illustrate another example predefined schedule of amplitude adjustments, which includes the same electrode combinations and steps as FIGS. 10A-10D. However, in FIGS. 11A-11D, the anodic amplitude setting are expressed as a percentage of an absolute current amplitude, and a cathodic amplitude settings are expressed as an amplitude at the respective cathode in the electrode combination. Although FIGS. 10A-10D illustrate adjustment increments of 10%, in other examples, other amplitude adjustment increments may be used, such as increments of about 4% or 6%. In addition, although FIGS. 11A-11D illustrate amplitude adjustment increments of 10% and 0.5 mA, other amplitude adjustment increments may be used.

Furthermore, the amplitude adjustment increments may be the same in each step of a predefined schedule in some examples, as shown in FIGS. 10A-11D. In other examples, at least two steps different amplitude adjustment increments. For example, the amplitude adjustment increments in FIGS. 10A-10D may alternate between 4% and 6% for subsequent steps in the schedule.

In some examples, the electrode combination scanning process may be transparent to a user. For example, programmer 18 may be configured to display information identifying the current electrode combination being tested on patient.

Figure 12:
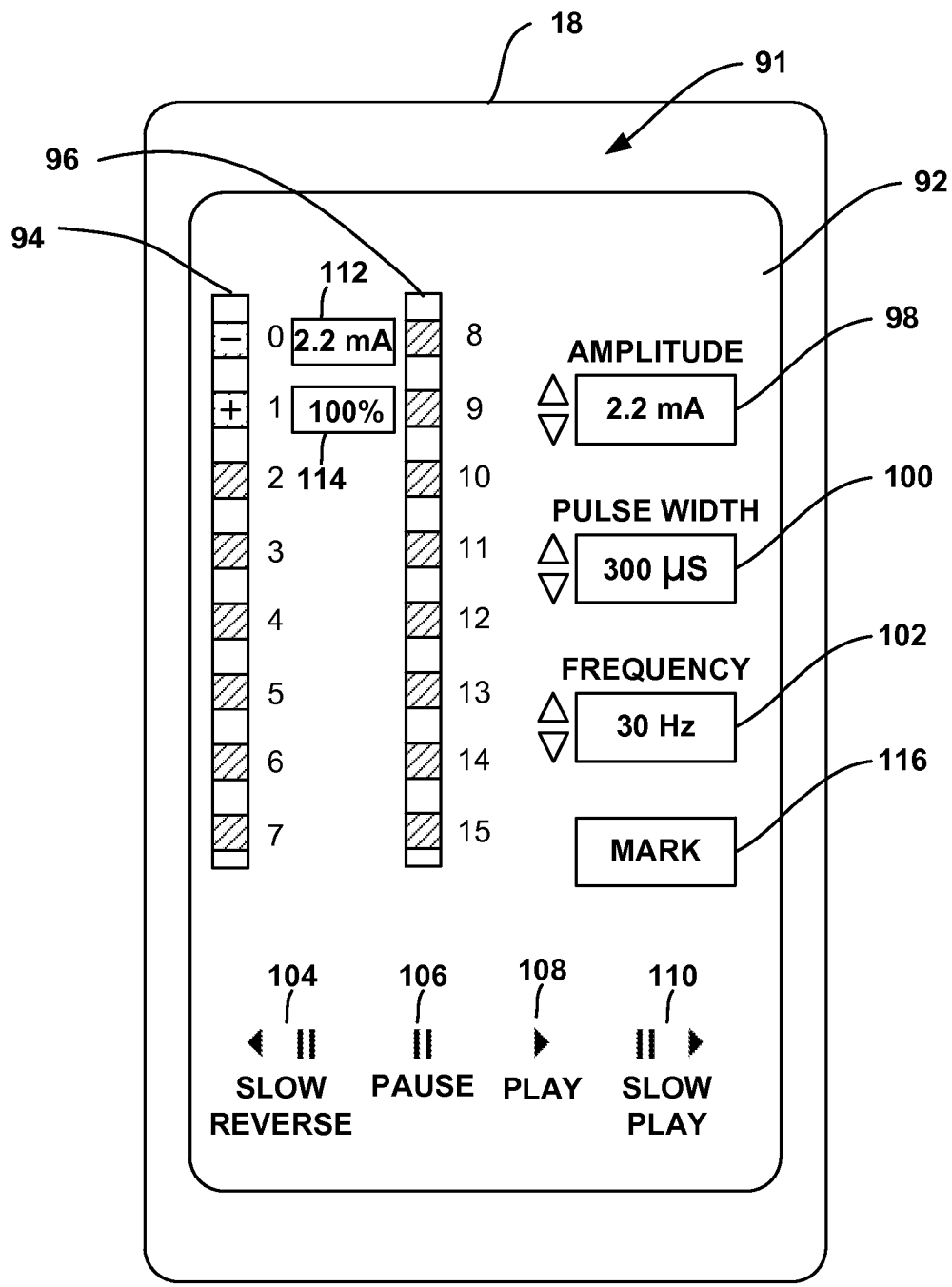
FIG. 12 is a schematic diagram illustrating an example graphical user interface (GUI) that may be generated and displayed by a programmer.

FIG. 12 is a schematic diagram illustrating an example GUI 91 that may be generated and displayed by programmer 18. Processor 60 may generate and present GUI 91 in order to help a clinician identify one or more efficacious electrode combinations, with which the clinician may define one or more therapy programs. In the example shown in FIG. 12, processor 60 of programmer 18 automatically selects the electrode combinations to be tested on patient 12 and transmits information to IMD 14, e.g., via the respective telemetry modules 64, 40, to control the delivery of test stimulation to patient 12 in accordance with the selected electrode combination. For example, for each electrode combination of the set tested on patient 12, processor 60 may transmit the parameters, e.g. amplitude, frequency, pulse width, and electrode combination, to IMD 14. In this manner, the order of electrode combinations can be stored on and managed by programmer 18, and not IMD 14. IMD 14 only receives definite parameter values from programmer 18 according to which IMD 14 delivers stimulation to patient 12. In other examples, the order of electrode combinations can be stored on and managed by processor 30 of IMD 14 alone or in combination with programmer 18.

In the example of FIG. 12, programmer 18 comprises a touch screen display 92 that presents GUI 91, which includes a number of user interface elements that represent leads and electrodes and electrical stimulation parameters. In some examples, as shown in FIG. 12, GUI 91 includes a graphical representation of pair of leads 94, 96, each including a set of eight electrodes. For example, a first lead 94 includes electrodes 0-7 and a second lead 96 includes electrodes 8-15. Leads 94, 96 may be graphical representations of, for example, leads 16 of system 10. The orientation of leads 94, 96 in GUI 91 is such that the distal end of each lead is at the top of the display. GUI 91 may schematically represents leads 94, 96 and respective electrodes as they generally are arranged implanted within patient 12, e.g., as two side-by-side leads arranged vertically and each including a number of electrodes, e.g., eight electrodes.

In some examples, as a preliminary step to identifying one or more efficacious electrode combinations, a user defines a lead configuration using programmer 18. For example, the user can select a lead type and configuration from a list of options, e.g. a lead including four or eight ring electrodes. Once the lead type is selected, the user can select the orientation of the lead on programmer display 92, e.g. orient the lead vertically or horizontally on the display 92. In some cases, a lead configuration including electrodes on two or three leads may be selected.

A user may interact with GUI 91 (e.g., by providing input using user interface 66 of programmer 18) to select stimulation parameter values for the test electrical stimulation and control the overall intensity of the stimulation delivered by IMD 14. For example, in the example shown in FIG. 12, GUI 91 includes an amplitude adjustment area 98, a pulse width adjustment area 100 and a frequency adjustment area 102. A user may increase or decrease the intensity of the stimulations by selecting or entering parameter information within areas 98, 100, 102. Processor 60 may control the stimulation parameters of the test stimulation energy delivered by IMD 14 based on the information within areas 98, 100, 102. As described above, in some examples, all or some of these stimulation parameters may be modified during the automatic testing of a set of electrode combinations, e.g., while the automatic testing is paused. In other examples, all or some of these stimulation parameters may only be modified before starting the automatic testing of the set of electrode combinations, e.g., outside of the automatic testing programming feature provided by programmer 18.

The amplitude displayed by area 98 may be, for example, an absolute current amplitude for the test electrical stimulation. The intensity of the electrical stimulation energy may be a function of the amplitude displayed by area 98.

A user may also interact with GUI 91 to initiate the automatic scan through the electrode combinations of a set, e.g., to initiate the automatic delivery of electrical stimulation by IMD 14 via electrode combinations of the set. In some examples, programmer 18 is configured to control IMD 14 to scan through (i.e., test) a plurality of different sets of electrode combinations, and the user may interact with GUI 91 to select a set of electrode combinations from the plurality of available sets before initiating the automatic scan. In other examples, programmer 18 is configured to control IMD 14 to automatically scan through a single set of electrode combinations. In this case, the user may only need to activate the programming tool in order to initiate the automatic scan.

In the example shown in FIG. 12, GUI 91 includes slow reverse button 104, pause button 106, play button 108, and slow play button 110, which may be graphical objects displayed by processor 60 and selectable by a user. A user may initiate the automatic scan along the electrodes of a lead 92 or 94 (or both leads 92, 94) by instructing programmer 18 to automatically "play" through electrode combinations of the set in the predefined order, according to a predefined schedule of amplitude adjustments (if implemented), and according to the stimulation parameters indicated by areas 98, 100, 102. For example, the clinician may press a play button 108, and, in response to receiving such input, processor 60 may instruct IMD 14 to initiate stimulation according to each electrode combination of the predefined set with the stimulation parameters selected by the clinician.

GUI 91 is configured to provide a number of controls for stopping or modifying the automatic scan through the set of electrode combinations. For example, the user may activate pause button 106 to pause the scan at any point during the course of the automatic scan through the set of electrode combinations (in the predetermined order). In response to receiving the input via pause button 106, processor 60 may instruct IMD 14 to stop the delivery of electrical stimulation. In other examples, in response to receiving the input via pause button 106, processor 60 may instruct IMD 14 to maintain the delivery of electrical stimulation via the currently selected electrode combination and anodic and cathodic amplitude settings, thereby stopping the changing of electrode combination and anodic and cathodic amplitude settings at the point at which pause button 106 was selected, but not stopping the delivery of electrical stimulation. Thus, in some examples, after the user has paused the scan, IMD 14 will continue to deliver stimulation to patient 12, but will no longer continue to scan through the set of electrode combinations.

While the automatic scan is paused, processor 60 is configured to restart the scan in response to receiving user input selecting play button 108 or selecting pause button 106 a second time. In response to detecting the re-initiation of the scan, processor 60 may instruct IMD 14 to resume the scan. In examples in which electrical stimulation was stopped in response to activation of the pause button 106, processor 60 may instruct IMD 14 to resume delivering electrical stimulation to patient 12 via the last-selected electrode combination, e.g., by restarting the time slot if the anodic and cathodic amplitude settings are modified according to a predefined schedule defining a plurality of time slots and associated anodic and cathodic amplitude settings. In examples in which electrical stimulation was maintained in response to activation of the pause button 106, processor 60 may instruct IMD 14 to continue delivering electrical stimulation to patient 12 via the last-selected electrode combination (and anodic and cathodic amplitude settings) for a new time slot, continue delivering electrical stimulation to patient 12 via the last-selected electrode combination for the remainder of the time slot started prior to the pause, or to switch to the next electrode combination in the order.

Processor 60 may also be configured to skip to a different electrode combination in the set in response to receiving user input. For example, as discussed above, the user may pause a scan by selecting pause button 106 and then select one of the displayed electrodes to select a new starting electrode for the scan. In response to receiving input selecting the new starting electrode, processor 60 may select a different electrode combination from the set, e.g., an electrode combination having a proximal-most active electrode at the starting electrode selected by the user, an electrode combination having a proximal-most cathode at the starting electrode, an electrode combination having a proximal-most anode at the starting electrode, or the like for distal-most positions.

As another example of how processor 60 may skip to a different electrode combination in the set, in some examples, the user may reverse backwards from the paused location through the set of electrode combinations in response to receiving input selecting skip backward button 104. Processor 60 may skip back one electrode combination in the predetermined order for each selection of slow reverse button 104. Activation of the reverse function provided by programmer 18 requires intervention by the user; that is, the reverse function is a manual process that requires the user to provide input to programmer 18, which then transmits commands to IMD 14. The reverse features of programmer 18 may enable a clinician to quickly revisit an electrode combination and respective anodic and cathodic amplitude settings, if desired.

Although not shown in FIG. 12, in some examples, GUI 91 also includes a skip forward button, which may provide a similar function as slow reverse button 104, but permits the user to skip to an electrode combination (and anodic and cathodic amplitude settings) at a later position in the order than the currently selected electrode combination and anodic and cathodic amplitude settings combination. The skip forward features of programmer 18 may enable a clinician to skip the testing of some electrode combinations in the set, e.g., if the electrode combinations are determined to be at axial positions of the lead that are not proximate a target tissue site, and, therefore, may not result in efficacious electrical stimulation, and/or skip some anodic and cathodic amplitude settings for a particular electrode combination.

Processor 60 may implement any suitable technique to transition between a currently selected electrode combination and the electrode combination to which the user wishes to skip forward or backward in the order. For example, processor 60 may transmit signals IMD 14 to cause stimulation generator 34 to reduce the electrical stimulation delivered via the starting electrode combination down to zero and then ramp up the stimulation delivered to via the destination electrode combination up from zero to the programmed intensity, such that each electrode combination is discretely selected and tested.

In the example shown in FIG. 12, GUI 91 also includes slow play button 110, which enables the user to continue the scan in the predetermined order but at a slower speed. In response to receiving the user input selecting button 110, processor 60 may change the rate at which the transition between electrode combinations and/or anodic and cathodic amplitude settings take place. The slower speed of the scan may allow for patient 12 to perceive the stimulation according to a particular electrode combination and anodic and cathodic amplitude setting for a longer period of time, which may be useful for evaluating the efficacy of the electrode combinations. Processor 60 may change the rate of transitions using any suitable technique, such as by adjusting the minimum amplitude adjustment increments or minimum percentage increments, or increasing the duration of time period between the application of each of the increments (also referred to herein as time slots). In some examples, processor 60 changes the rate of transitions in response to user input. For example, processor 60 may generate and present a set-up screen prior to initiating the automatic scan through a set of electrode combinations, and the set-up screen may present the user with options to set the speed of transitions between electrode combinations, e.g., based on what may be comfortable for the particular patient.

In each of the different user inputs described above that results in selection of a different electrode combination in the set, processor 60 maintains the selection of the next electrode combination/amplitude adjustment to test on patient 12 based on the predetermined order. Programmer 18 can be configured such that the user cannot modify the order in which the electrode combinations are tested on patient 12. In addition, processor 60 may be configured to limit some user-specified movements, such as movements that would lead to the overall output limit of IMD 12 being exceeded or if the movement would result in a relatively high amount of electrical stimulation delivered to patient 12 via one electrode.

GUI 91 may include a stop button, a save & end button, or both, in addition to or instead of slow reverse button 104, pause button 106, play button 108, and slow play button 110. The stop button may end the testing of the set of electrode combinations, and the save & end button may end the testing of the electrode combinations and save any input (e.g., user input marking one or more electrode combinations and associated anodic and cathodic amplitude settings) received during the testing. In either case, the stop button may permit the play button 108 to be inactivated, and the user may provide input adjusting other settings (e.g., adjusting the amplitude or other stimulation parameter values).

In some examples, programmer 18 may be configured to receive user input in another manner. For example, GUI 91 may not include one or more of slow reverse button 104, pause button 106, play button 108, or slow play button 110. As another example, programmer 18 can include, as part of GUI 91 or a physical input mechanism, other input devices, such as a scroll wheel.

Programmer 18 is configured to display information about the electrode combination being tested on patient 12. For example, after the automatic scanning through electrode combinations of a set is initiated, processor 60 may update the graphical representation of the electrodes of leads 94, 96 to reflect the electrode combination with which IMD 14 is currently delivering electrical stimulation to patient 12. For example, processor 60 may update GUI 91 so that the active electrodes of the electrode combination are associated with a polarity symbol, minus, "−," for cathodes and plus, "+," for anodes. The user may view this displayed graphical representation of the electrode combination and quickly ascertain the electrode combination that is currently being tested on patient 12.

Processor 60 may also present, via GUI 91, information about the anodic and cathodic amplitude settings, the intensity of the electrical stimulation energy being delivered via the displayed electrode combinations, or both. In the example shown in FIG. 12, each active electrode of the electrode combination currently selected by processor 60 is associated with a text box that includes a numerical value relating to the stimulation intensity with which the respective electrode is programmed and/or is currently applying stimulation. Each cathode electrode can be associated with a text box that indicates the stimulation amplitude value according to which that cathode is programmed and is currently applying stimulation to patient 12. In some examples, each cathode electrode also includes a percentage that reflects the current distribution to the electrode as a percentage of the total current delivered to all the cathodes of the electrode combination.

Each anode electrode can be associated with a text box that indicates a percentage that reflects the current distribution to the electrode as a percentage of the total current delivered to all the anodes in the electrode combination. The percentage current distribution for cathodes and anodes does not change as stimulation amplitude is ramped up or down, e.g., based on user input provided via adjustment areas 98, 100, 102. The amplitude of cathodes presented in the associated text boxes, however, can be a reflection of the actual stimulation current level applied and thus will increase or decrease with stimulation applied by IMD 14 via the respective electrode. The anodic and cathodic amplitude settings indicated by the text boxes may illustrate, in real time, the transition between subsequently tested electrode combinations.

As the intensity of electrical stimulation is increased or decreased, e.g., based on user input, during delivery of electrical stimulation by IMD 14 with the displayed electrode combination, the graphical display of the active electrodes may change to reflect the state of the applied stimulation. For example, processor 60 can update the amplitude in the text box associated with a particular cathode of the electrode combination to reflect the intensity of the stimulation currently being applied by IMD 14 via that cathode.

In some examples, processor 60 may also associate a graphic (not shown in FIG. 12) with the active electrodes, and modify the size of the graphic as a function of the amplitude of the currently applied stimulation. For example, as IMD 14 increases the stimulation applied to patient 12, processor 60 may modify GUI 91 to reflect the changing stimulation by increasing the size of the graphics representing the relative amplitudes of the stimulation currently applied via each respective electrode. The graphics can be, for example, circles or another two dimensional graphics overlaying respective electrodes of the electrode combination. The graphics may be another visual aid with which the user may quickly ascertain the electrode combination and anodic and cathodic amplitude settings being tested on patient 12.

In the example shown in FIG. 12, GUI 91 includes mark button 116, which the user may select to mark the electrical combination and associated amplitudes currently displayed by GUI 91 and currently being used by IMD 14 to deliver electrical stimulation to patient 12. Processor 60 may receive input via mark button 116 when a user determines that a particular setting is efficacious. As discussed above, in response to receive the input from user via mark button 116, processor 60 may generate a marker and associate the marker (e.g., in memory 62 or another memory) with the electrode combination and, in some examples, the anodic and cathodic amplitude settings, implemented by IMD 14 at the time the user provided the input. In some examples, processor 60 also stores the other parameter values (indicated by inputs 98, 100, 102) with the marker and associated electrode combination. In this way, the user can later retrieve the marked electrode combinations and determine the stimulation parameter values that resulted in the efficacious electrode combination.

Although example electrode combination identification devices, systems, and techniques have been described with respect to selecting electrode combinations of a single lead 16A having eight electrodes 24, in other examples, the devices, systems, and techniques described herein may be used to identify desirable combinations of electrodes within electrode sets that are configured in any way, and used to provide any type of electrical therapy. The electrode sets may include electrodes carried by one lead, two leads, or a device housing.

For example, if system 10 includes multiple columns of electrodes, whether on a single lead 16A or 16B or defined by two or more leads 16, a set of test electrode combinations can include electrode combinations including electrodes from two or more columns of electrodes. As another example, each of the electrode combinations of the set may include electrodes from a single column of electrodes, but the set of electrode combinations may include test electrode combinations for two or more columns. In some examples, the electrode combinations may be ordered in the set such that electrode combinations on a first column of electrodes are tested, followed by electrode combinations on a second column of electrodes (e.g., immediately adjacent to the first column).

For example, a set of test electrode combinations can include a plurality of electrode combinations that include electrodes from both leads 16. Each electrode combination may only include electrodes from one lead 16, and the electrode combinations can be arranged such that electrode combinations of a first lead 16A are scanned, followed by the electrode combinations of a second lead 16B. In this example, the electrode combinations may be arranged in a predetermined order such that adjacent electrode combinations share at least one anode electrode or at least one cathode electrode, with the exception of adjacent electrode combinations that include electrodes of different leads.

Electrode combinations including electrode combinations on both leads 16 may also be part of a set of electrode combinations tested on patient 12. Even in this example, electrode combinations of a predefined set may be arranged in a predetermined order such that adjacent electrode combinations share at least one anode electrode or at least one cathode electrode, and, in some examples, such that all electrode combinations include adjacent active electrodes uninterrupted by inactive electrodes.

Although each of the sets of electrode combinations described herein includes multipolar electrode combinations (including both anode and cathode electrodes), in some examples, the devices, systems, and techniques described herein may also be used to test a set of unipolar electrode combinations on patient 12. The unipolar electrode combinations may still be arranged such that adjacent electrode combinations (e.g., defined by electrodes on a lead) share at least one cathode electrode.

The techniques described in this disclosure, including those attributed to IMD 14, programmer 18, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

For example, the electrode combination testing features described herein, e.g., the control of delivery of electrical stimulation by IMD 14 according to each electrode combination of a set of electrode combinations in a predetermined order, may be embedded as a single function within a full featured programmer 18. The programmer may include the option to program parameters incorporating traditional programming tools, as well as the diagnostic, measurement, and other features necessary to manage IMD 14. In other examples, the electrode combination testing features could be deployed as a stand alone tool in a programmer 18. Moreover, the shifting process may be executed by IMD 14 in response to instructions from programmer 18 during a programming session, in response to instructions from programmer 18 during ordinary, chronic usage of IMD 14 by patient 12, or in response to instructions generated by processor 30 of IMD 14 itself.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. Instructions may be executed by one or more processors, such as one or more DSPs, ASICs, FPGAs, general purpose microprocessors, or other equivalent integrated or discrete logic circuitry.

Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A method comprising:
   with one or more processors, selecting a predefined set of electrode combinations, wherein each electrode combination of the predefined set includes one or more anode electrodes and one or more cathode electrodes, a relative arrangement of the one or more anodes and the one or more cathodes defining an electrode pattern of the electrode combination; and
   with the one or more processors, automatically controlling a medical device to deliver, in a predetermined order, electrical stimulation to a patient via each electrode combination of the predefined set of electrode combinations, wherein the electrode combinations in the predetermined order define a repeating sequence of electrode patterns.

2. The method of claim 1, wherein automatically controlling the medical device to deliver the electrical stimulation comprises controlling the medical device to deliver electrical stimulation according to a predefined sequence of amplitude adjustments that defines the predefined set of electrode combinations, the predefined sequence of amplitude adjustments including a plurality of steps and, for each step, active electrodes used by the medical device for delivery of electrical stimulation therapy, and, for each of the active electrodes, an anodic amplitude setting or a cathodic amplitude setting.

3. The method of claim 2, wherein controlling the medical device according to the predefined sequence of amplitude adjustments comprises controlling the medical device to transition between successive steps of the predefined sequence by at least increasing or decreasing at least one of the anodic amplitude or the cathodic amplitude for at least one active electrode by an amplitude adjustment increment, wherein the amplitude adjustment increments are substantially the same between successive steps of the predefined sequence.

4. The method of claim 2, wherein controlling the medical device according to the predefined sequence of amplitude adjustments comprises controlling the medical device to transition between successive steps of the predefined sequence by at least increasing or decreasing at least one of the anodic amplitude or the cathodic amplitude for at least one active electrode by an amplitude adjustment increment, wherein the predefined sequence includes at least two different amplitude adjustment increments, and wherein controlling the medical device to transition between successive steps of the predefined sequence comprises increasing or decreasing at least one of the anodic amplitude or the cathodic amplitude for at least one active electrode by one amplitude adjustment increment of the at least two different amplitude adjustment increments.

5. The method of claim 2, wherein the predefined sequence includes two different amplitude adjustment increments, wherein increasing or decreasing the at least one of the anodic amplitude or the cathodic amplitude for the at least one active electrode is by an amplitude adjustment increment of the two different amplitude adjustment increments that alternates between successive steps of the predefined sequence.

6. The method of claim 1, wherein the electrode patterns include a first simple bipole, a second simple bipole, a guarded cathode, and a guarded double cathode.

7. The method of claim 1, further comprising selecting an electrode combination from the predefined set of electrode combinations based on the delivery of the electrical stimulation by the medical device.

8. The method of claim 1, wherein the electrode combinations are defined by subsets of electrodes of an electrical stimulation lead, and wherein controlling the medical device to deliver, in the predetermined order, electrical stimulation to the patient via each electrode combination of the predefined set of electrode combinations comprises controlling the medical device to deliver electrical stimulation to the patient via at least two electrode patterns at two different axial positions along the electrical stimulation lead.

9. The method of claim 1, wherein the electrode combinations are defined by subsets of electrodes of an electrical stimulation lead, wherein the electrode combinations are arranged in the predetermined order such that electrode combinations are propagated along the electrical stimulation lead.

10. The method of claim 1, further comprising:
    receiving a first user input;
    controlling the medical device to one of pause delivering electrical stimulation or continue delivering electrical stimulation according to a currently selected electrode combination of the predefined set of electrode combinations in response to receiving the first user input;
    subsequently receiving a second user input; and
    controlling the medical device to transition from the currently selected electrode combination to a next electrode combination in the predetermined order in response to receiving the second user input.

11. The method of claim 1, further comprising:
    receiving user input selecting a starting electrode;
    selecting a starting electrode combination from the predefined set of electrode combinations based on the starting electrode selected by the user; and
    automatically controlling the medical device to deliver electrical stimulation to the patient via the starting electrode combination and electrode combinations of the predefined set of electrode combinations following the starting electrode combination in the predetermined order.

12. The method of claim 1, further comprising:
    receiving user input; and
    modifying the predefined set of electrode combinations in response to receiving the user input.

13. The method of claim 1, wherein controlling the medical device to deliver electrical stimulation to the patient via the predefined set of electrode combinations in the predetermined order comprises controlling the medical device to transition between a first electrode combination and a second electrode combination adjacent to the first electrode combination in the predetermined order by at least incrementally adjusting at least one of anodic amplitudes assigned to anodes of the first electrode combination or cathodic amplitudes assigned to cathodes of the first electrode combination.

14. The method of claim 1, wherein at least one of the electrode combinations of the predefined set is defined by a subset of electrodes of an electrical stimulation lead.

15. The method of claim 1, wherein at least one of the electrode combinations of the predefined set is defined by an electrode of a housing of the medical device and at least one electrode of an electrical stimulation lead.

16. A system comprising:
a medical device,
a plurality of electrodes; and
a processor configured to control the medical device to deliver, in a predetermined order, electrical stimulation to a patient via each electrode combination of a predefined set of electrode combinations, wherein the electrode combinations of the predefined set of electrode combinations are defined by subsets of electrodes of the plurality of electrodes, wherein each electrode combination of the predefined set includes one or more anode electrodes and one or more cathode electrodes, a relative arrangement of the one or more anodes and the one or more cathodes defining an electrode pattern of the electrode combination, and wherein the electrode combinations in the predetermined order define a repeating sequence of electrode patterns.

17. The system of claim 16, wherein the processor is configured to control the medical device to deliver the electrical stimulation by at least controlling the medical device to deliver electrical stimulation according to a predefined sequence of amplitude adjustments that defines the predefined set of electrode combinations, the predefined sequence of amplitude adjustments including plurality of steps and, for each step, active electrodes used by the medical device for delivery of electrical stimulation therapy, and, for each of the active electrodes, an anodic amplitude setting or a cathodic amplitude setting.

18. The system of claim 17, wherein the processor is configured to control the medical device according to the predefined sequence of amplitude adjustments by at least controlling the medical device to transition between successive steps of the predefined sequence by at least increasing or decreasing at least one of the anodic amplitude or the cathodic amplitude for at least one active electrode by an amplitude adjustment increment, wherein the amplitude adjustment increments are substantially the same between successive steps of the predefined sequence.

19. The system of claim 17, wherein the processor is configured to control the medical device according to the predefined sequence of amplitude adjustments by at least controlling the medical device to transition between successive steps of the predefined sequence by at least increasing or decreasing at least one of the anodic amplitude or the cathodic amplitude for at least one active electrode by an amplitude adjustment increment, wherein the predefined sequence includes at least two different amplitude adjustment increments, and wherein controlling the medical device to transition between successive steps of the predefined sequence comprises increasing or decreasing at least one of the anodic amplitude or the cathodic amplitude for at least one active electrode by one amplitude adjustment increment of the at least two different amplitude adjustment increments.

20. The system of claim 17, wherein the predefined sequence includes two different amplitude adjustment increments, wherein increasing or decreasing the at least one of the anodic amplitude or the cathodic amplitude for the at least one active electrode is by an amplitude adjustment increment of the two different amplitude adjustment increments that alternates between successive steps of the predefined sequence.

21. The system of claim 16, wherein the electrode patterns include a first simple bipole, a second simple bipole, a guarded cathode, and a guarded double cathode.

22. The system of claim 16, wherein the processor is configured to select an electrode combination from the predefined set of electrode combinations based on the delivery of the electrical stimulation by the medical device.

23. The system of claim 16, further comprising an electrical stimulation lead comprising the plurality of electrodes, wherein the processor is configured to control the medical device to deliver, in the predetermined order, electrical stimulation to the patient via each electrode combination of the predefined set of electrode combinations by at least controlling the medical device to deliver electrical stimulation to the patient via at least two electrode patterns at two different axial positions along the electrical stimulation lead.

24. The system of claim 16, further comprising an electrical stimulation lead comprising the plurality of electrodes, wherein the electrode combinations are arranged in the predetermined order such that electrode combinations are transitioned along the electrical stimulation lead.

25. The system of claim 16, further comprising a user interface, wherein the processor is configured to receive a first user input via the user interface, control the medical device to one of pause electrical stimulation or continue delivering electrical stimulation according to a currently selected electrode combination of the predefined set of electrode combinations in response to receiving the first user input, subsequently receive a second user input, and control the medical device to transition from the currently selected electrode combination to a next electrode combination in the predetermined order in response to receiving the second user input.

26. The system of claim 16, further comprising a user interface, wherein the processor is configured to receive user input selecting a starting electrode via the user interface, select a starting electrode combination from the predefined set of electrode combinations based on the starting electrode selected by the user, and automatically control the medical device to deliver, in the predetermined order, electrical stimulation to the patient via the starting electrode combination and each electrode combination of the predefined set of electrode combinations following the starting electrode combination in the predetermined order.

27. The system of claim 16, further comprising a user interface, wherein the processor is configured to receive user input via the user interface and modify the predefined set of electrode combinations in response to receiving the user input.

28. The system of claim 16, wherein the processor is configured to control the medical device to deliver, in the predetermined order, electrical stimulation to the patient via each electrode combination of the predefined set of electrode combinations by at least controlling the medical device to transition between a first electrode combination and a second electrode combination adjacent to the first electrode combination in the order by incrementally adjusting at least one of anodic amplitudes assigned to anodes of the first electrode combination or cathodic amplitudes assigned to cathodes of the first electrode combination.

29. The system of claim 17, further comprising a memory that stores the predefined sequence of amplitude adjustments.

30. The system of claim 16, wherein the medical device comprises the processor.

31. The system of claim 16, further comprising a medical device programmer that comprises the processor.

32. The system of claim 16, further comprising an electrical stimulation lead comprising the plurality of electrodes.

33. The system of claim 16, wherein the medical device comprising a housing including a housing electrode, wherein at least one of the electrode combinations of the predefined set is defined by the housing electrode and at least one electrode of an electrical stimulation lead.

34. A system comprising:
    means for delivering electrical stimulation to a patient; and
    means for controlling the means for delivering electrical stimulation to deliver, in a predetermined order, electrical stimulation to the patient via each electrode combination of a predefined set of electrode combinations, wherein each electrode combination of the predefined set includes one or more anode electrodes and one or more cathode electrodes, a relative arrangement of the one or more anodes and the one or more cathodes defining an electrode pattern of the electrode combination, and wherein the electrode combinations in the predetermined order define a repeating sequence of electrode patterns.

35. The system of claim 34, wherein the means for controlling controls the means for delivering according to a predefined sequence of amplitude adjustments that defines the predefined set of electrode combinations, the predefined sequence of amplitude adjustments including plurality of steps and, for each step, active electrodes used by the medical device for delivery of electrical stimulation therapy, and, for each of the active electrodes, an anodic amplitude setting or a cathodic amplitude setting.

36. A non-transitory computer-readable storage medium comprising instructions that, when executed by a processor, cause the processor to:
    control a medical device to deliver, in a predetermined order, electrical stimulation to a patient via each electrode combination of a predefined set of electrode combinations, wherein each electrode combination includes one or more anode electrodes and one or more cathode electrodes, a relative arrangement of the one or more anodes and the one or more cathodes defining an electrode pattern of the electrode combination, and wherein the electrode combinations in the predetermined order define a repeating sequence of electrode patterns; and
    select an electrode combination from the predefined set of electrode combinations based on the delivery of the electrical stimulation by the medical device.

37. The non-transitory computer-readable storage medium of claim 36, wherein the instructions, when executed by the processor, cause the processor to control the medical device to deliver the electrical stimulation by at least controlling the medical device according to a predefined sequence of amplitude adjustments that defines the predefined set of electrode combinations, the predefined sequence of amplitude adjustments including plurality of steps and, for each step, active electrodes used by the medical device for delivery of electrical stimulation therapy, and, for each of the active electrodes, an anodic amplitude setting or a cathodic amplitude setting.

* * * * *